United States Patent
Rigoli et al.

(10) Patent No.: US 10,111,432 B2
(45) Date of Patent: *Oct. 30, 2018

(54) PICOLINAMIDE N-OXIDE COMPOUNDS WITH FUNGICIDAL ACTIVITY

(71) Applicant: Dow AgroSciences LLC, Indianapolis, IN (US)

(72) Inventors: Jared W. Rigoli, Indianapolis, IN (US); Kevin G. Meyer, Zionsville, IN (US); Chenglin Yao, Westfield, IN (US); Brian A. Loy, Indianapolis, IN (US); Brannon Sam, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/690,866

(22) Filed: Aug. 30, 2017

(65) Prior Publication Data
US 2018/0055053 A1   Mar. 1, 2018

Related U.S. Application Data

(60) Provisional application No. 62/381,259, filed on Aug. 30, 2016, provisional application No. 62/381,268, filed on Aug. 30, 2016, provisional application No. 62/381,273, filed on Aug. 30, 2016, provisional application No. 62/381,279, filed on Aug. 30, 2016, provisional application No. 62/381,287, filed on Aug. 30, 2016, provisional application No. 62/381,285, filed on Aug. 30, 2016, provisional application No. 62/381,280, filed on Aug. 30, 2016, provisional application No. 62/381,282, filed on Aug. 30, 2016.

(51) Int. Cl.
*A01N 43/40*   (2006.01)
*C07D 213/89*   (2006.01)
*A01N 43/90*   (2006.01)
*C07D 213/81*   (2006.01)
*C07D 213/83*   (2006.01)

(52) U.S. Cl.
CPC ............. *A01N 43/40* (2013.01); *A01N 43/90* (2013.01); *C07D 213/81* (2013.01); *C07D 213/83* (2013.01); *C07D 213/89* (2013.01)

(58) Field of Classification Search
CPC .............................. A01N 43/40; C07D 213/89
See application file for complete search history.

(56) References Cited

U.S. PATENT DOCUMENTS 4,832,729 A * 5/1989 Shigematsu ........... A01N 43/54
                                                         504/230

FOREIGN PATENT DOCUMENTS

WO   WO-0105769 A2 *  1/2001  ............. A01N 43/40
WO   WO-2016109257 A1 *  7/2016  ............. A01N 37/44

* cited by examiner

*Primary Examiner* — Theodore R. West

(57) ABSTRACT

This disclosure relates to picolinamide N-oxides of Formula I and their use as fungicides.

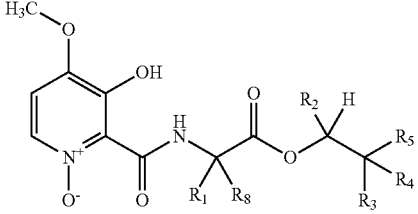

9 Claims, No Drawings

PICOLINAMIDE N-OXIDE COMPOUNDS WITH FUNGICIDAL ACTIVITY

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to picolinamide N-oxides and their use as fungicides. The compounds of the present disclosure may offer protection against ascomycetes, basidiomycetes, deuteromycetes and oomycetes.

One embodiment of the present disclosure may include compounds of Formula I:

I in which:

$R_1$ is hydrogen or $C_1$-$C_5$ alkyl, each optionally substituted with 0, 1 or multiple $R_6$;

$R_2$ is hydrogen, $C_1$-$C_5$ alkyl or cycloalkyl, each optionally substituted with 0, 1 or multiple $R_6$;

$R_3$ is alkyl, cycloalkyl, aryl, or heteroaryl, each optionally substituted with 0, 1 or multiple $R_6$;

$R_4$ is hydrogen, halo, hydroxyl, alkyl, or alkoxy;

$R_5$ is alkyl, cycloalkyl, aryl, heteroaryl, alkoxy, aryloxy, heteroaryloxy, each optionally substituted with 0, 1 or multiple $R_6$;

$R_6$ is hydrogen, alkyl, aryl, acyl, halo, alkoxy, or heterocyclyl, each optionally substituted with 0, 1 or multiple $R_7$;

$R_7$ is hydrogen, alkyl, aryl, acyl, halo, alkoxy, or heterocyclyl; and $R_8$ is hydrogen or $C_1$-$C_5$ alkyl, each optionally substituted with 0, 1 or multiple $R_6$.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl, and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "alkynyl" refers to a branched or unbranched carbon chain containing one or more triple bonds including, but not limited to, propynyl, butynyl, and the like.

The terms "aryl" and "Ar" refer to any aromatic ring, mono- or bi-cyclic, containing 0 heteroatoms.

The term "heterocyclyl" refers to any aromatic or non-aromatic ring, mono- or bi-cyclic, containing one or more heteroatoms.

The term "alkoxy" refers to an —OR substituent.

The term "acyloxy" refers to an —OC(O)R substituent.

The term "cyano" refers to a —C≡N substituent.

The term "hydroxyl" refers to an —OH substituent.

The term "amino" refers to a —N(R)$_2$ substituent.

The term "arylalkoxy" refers to —O(CH$_2$)$_n$Ar where n is an integer selected from the list 1, 2, 3, 4, 5, or 6.

The term "haloalkoxy" refers to an —OR—X substituent, wherein X is Cl, F, Br, or I, or any combination thereof.

The term "haloalkyl" refers to an alkyl, which is substituted with Cl, F, I, or Br or any combination thereof.

The term "halogen" or "halo" refers to one or more halogen atoms, defined as F, Cl, Br, and I.

The term "nitro" refers to a —NO$_2$ substituent.

The term thioalkyl refers to an —SR substituent.

Throughout the disclosure, reference to the compounds of Formula I is read as also including all stereoisomers, for example diastereomers, enantiomers, and mixtures thereof. In another embodiment, Formula I is read as also including salts or hydrates thereof. Exemplary salts include, but are not limited to: hydrochloride, hydrobromide, hydroiodide, trifluoroacetate, and trifluoromethane sulfonate.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and ampho-teric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting, and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulfosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis, Bacillus subtilis* strain QST713, benalaxyl, benomyl, benthiavalicarb-isopropyl, benzovindiflupyr, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), coumoxystrobin, cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dipymetitrone, dithianon, dodemorph, dodemorph acetate, dodine, dodine free base, edifenphos, enestrobin, enestroburin, enoxastrobin, epoxiconazole, ethaboxam, ethoxyquin, etridiazole, famoxadone, fenamidone, fenaminostrobin, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flufenoxystrobin, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isofetamid, isoprothiolane, isopyrazam, isotianil, kasugamycin, kasugamycin hydrochloride hydrate, kresoxim-methyl, laminarin, mancopper, mancozeb, mandestrobin, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxathiapiprolin, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picarbutrazox, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyraziflumid, pyrazophos, pyribencarb, pyributicarb, pyrifenox, pyrimethanil, pyriofenone, pyrisoxazole, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolprocarb, tolylfluanid, triadimefon, triadimenol, triazoxide, triclopyricarb, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)-N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril, benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb, prothiocarb hydrochloride, pyracarbolid, pyridinitril, pyroxychlor, pyroxyfur, quinacetol, quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, afidopyropen, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, broflanilide, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, clacyfos, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclaniliprole, cyclethrin, cycloprothrin, cyfluthrin, cyhalothrin, cypermethrin, cyphenothrin, cyromazine, cythioate, DDT, decarbofuran, deltamethrin, demephon, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicloromezotiaz, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinexdiclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepallethrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flometoquin, flonicamid, flubendiamide, flucofuron, flucycloxuron, flucythrinate, flufenerim, flufenoxuron, flufenprox, flufiprole, fluhexafon, flupyradifurone, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptafluthrin, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kappa-bifenthrin, kappa-tefluthrin, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, momfluorothrin, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyflubumide, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyriminostrobin, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, tetraniliprole, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tioxazafen, tolfenpyrad, tralomethrin, transfluthrin, transpermethrin, triarathene, triazamate, triazophos, trichlorfon, trichlormetaphos-3, trichloronat, trifenofos, triflumezopyrim, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenquinotrione, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halauxifen, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiafenacil, tiocarbazil, tioclorim, tolpyralate, topramezone, tralkoxydim, triafamone, tri-allate, triasulfuron, triaziflam, tribenuron, tricamba, triclopyr, tridiphane, trietazine, trifloxysulfuron, trifludimoxazin, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those skilled in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Zymoseptoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Pyricularia oryzae*), rust of soybean (*Phakopsora pachyrhizi*), glume blotch of wheat (*Leptosphaeria nodorum*), powdery mildew of wheat (*Blumeria graminis* f. sp. *tritici*), powdery mildew of barley (*Blumeria graminis* f. sp. *hordei*), powdery mildew of cucurbits (*Erysiphe cichoracearum*), anthracnose of cucurbits (*Colletotrichum lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, g/m²).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following scheme illustrates an approach to generating picolinamide N-oxide compounds of Formula I. The following description and example is provided for illustrative purposes and should not be construed as limiting in terms of substituents or substitution patterns.

Compounds of Formula I wherein $R_1$, $R_2$, $R_3$, $R_4$, $R_5$, and $R_8$ are as originally defined, can be prepared according to the method outlined in Scheme 1, step a. Compounds of Formula 1.0 wherein $R_1$, $R_2$, $R_3$, $R_4$, $R_5$, and $R_8$ are as originally defined, can be prepared as described by the procedures outlined in US patent applications WO 2016/109289, WO 2016/109257, and WO 2016/109302. Compounds of Formula 1.0 can be treated with an oxidizing reagent such as m-chloroperbenzoic acid (mCPBA) in a polar solvent such as dichloromethane ($CH_2Cl_2$), at a temperature of about 0° C. to 50° C. to afford compounds of Formula I, wherein $R_1$, $R_2$, $R_3$, $R_4$, $R_5$, and $R_8$ are as originally defined, as shown in a. It will be understood by those skilled in the art that compounds such as Formula I may also be prepared using other oxidizing agents including, but not limited to: hydrogen peroxide, hydrogen peroxide-urea complex, magnesium monoperoxyphthalate hexahydrate (MMPP), peroxyacetic acid, oxone, sodium perchlorate or dimethyl dioxirane.

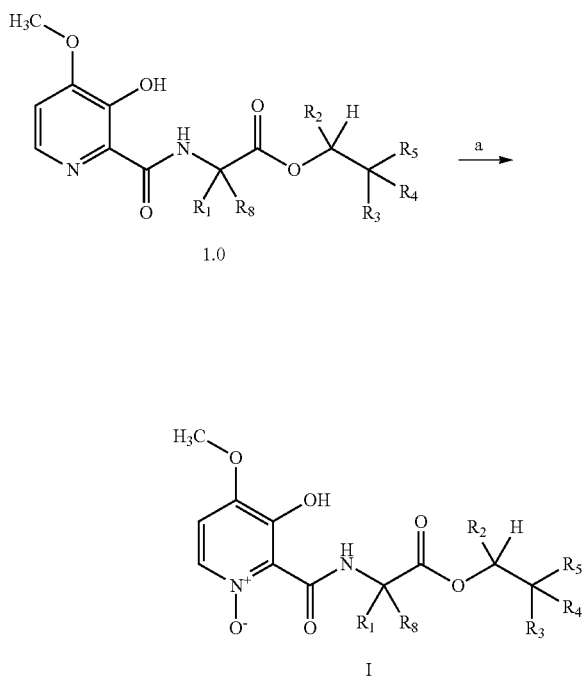

Scheme 1

EXAMPLES

Example 1: Preparation of 2-(((S)-1-(((S)-1,1-bis(2,4-dimethylphenyl)propan-2-yl)oxy)-1-oxopropan-2-yl)carbamoyl)-3-hydroxy-4-methoxypyridine 1-oxide. Compound 1

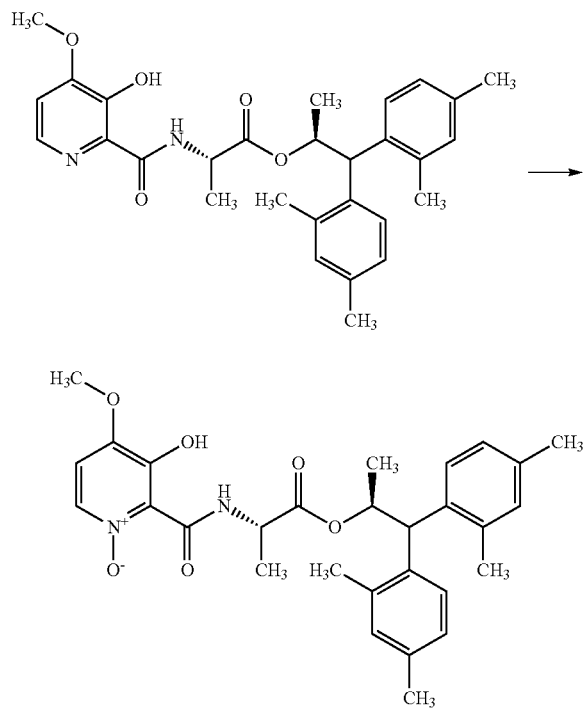 [SMILES: COc1ccnc(C(=O)N[C@@H](C)C(=O)O[C@@H](C)C(c2ccc(C)cc2C)c2ccc(C)cc2C)c1O ; COc1cc[n+]([O-])c(C(=O)N[C@@H](C)C(=O)O[C@@H](C)C(c2ccc(C)cc2C)c2ccc(C)cc2C)c1O]

To a solution of (S)-1,1-bis(2,4-dimethylphenyl)propan-2-yl (3-hydroxy-4-methoxypicolinoyl)-L-alaninate (WO 2016/109257) (0.025 g, 0.051 mmol) in $CH_2Cl_2$ (0.51 mL) was added m-chloroperbenzoic acid (≤70%, 0.025 g, 0.102 mmol). The mixture was stirred at room temperature overnight. The mixture was concentrated under reduced pressure and the crude residue was purified via flash chromatography (4 g silica column) using a 0-45% acetone/hexanes mixture as the eluent to provide the title compound (21 mg, 80% yield) as a white foam. $^1$H NMR (500 MHz, $CDCl_3$) δ 14.31 (s, 1H), 12.64 (d, J=7.0 Hz, 1H), 7.85 (d, J=7.2 Hz, 1H), 7.17 (d, J=7.9 Hz, 1H), 7.11 (d, J=7.7 Hz, 1H), 6.98-6.88 (m, 3H), 6.80 (s, 1H), 6.75 (d, J=7.1 Hz, 1H), 5.67 (dq, J=10.2, 6.1 Hz, 1H), 4.52-4.38 (m, 2H), 3.96 (s, 3H), 2.35 (s, 3H), 2.28 (s, 3H), 2.24 (s, 3H), 2.20 (s, 3H), 1.30 (d, J=6.2 Hz, 3H), 1.11 (d, J=7.2 Hz, 3H). IR (thin film) 2934, 1736, 1644, 1569, 1533, 1480, 1454, 1301, 1207, 1155, 1030, 911, 808, 733 $cm^{-1}$. ESIMS m/z 507.2 [(M+H)+].

Compound structures, appearance, and preparation methods of compound of the present disclosure are shown below in Table 1. Analytical data for compounds shown in Table 1 is shown below in Table 2.

Example A: Evaluation of Fungicidal Activity: Leaf Blotch of Wheat (*Zymoseptoria tritici*; Bayer Code SEPTTR)

Technical grades of materials were dissolved in acetone, which were then mixed with nine volumes of water ($H_2O$) containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases, unless stated otherwise. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Zymoseptoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the $1^{st}$ leaves of untreated plants, infection levels were assessed on a scale of 0 to 100 percent disease severity. Percent disease control was calculated using the ratio of disease severity on treated plants relative to untreated plants. Results of the evaluations are shown below in Table 4.

Example B: Evaluation of Fungicidal Activity: Wheat Brown Rust (*Puccinia triticina*; Synonym: *Puccinia recondita* f. sp. *tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A. Results of the evaluations are shown below in Table 4.

Example C: Evaluation of Fungicidal Activity: Asian Soybean Rust (*Phakopsora pachyrhizi*; Bayer Code PHAKPA)

Technical grades of materials were dissolved in acetone, which were then mixed with nine volumes of $H_2O$ containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 3 days prior to or 1 day after fungicide treatments. Plants were incubated for 24 h in a dark dew room at 22° C. and 100% relative humidity then transferred to a growth room at 23° C. for disease to develop. Disease severity was assessed on the sprayed leaves. Results of the evaluations are shown below in Table 5.

TABLE 1

| | Compound Structure, Preparation Method, and Appearance | | |
|---|---|---|---|
| Cmpd. No. | Structure | As Prepared According To | Appearance |
| 1 | (structure) | WO 2016/109257 Example 1 | White Foam |
| 2 | (structure) | WO 2016/109257 Example 1 | White Foam |
| 3 | (structure) | WO 2016/109257 Example 1 | White Foam |
| 4 | (structure) | WO 2016/109257 Example 1 | White Foam |

TABLE 1-continued

Compound Structure, Preparation Method, and Appearance

| Cmpd. No. | Structure | As Prepared According To | Appearance |
|---|---|---|---|
| 5 | 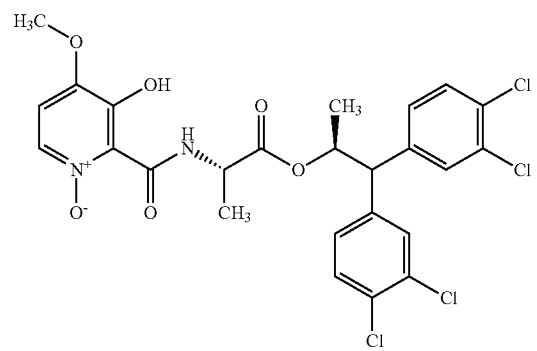 [SMILES: COc1cc[n+]([O-])c(C(=O)N[C@@H](C)C(=O)O[C@@H](C)C(c2ccc(Cl)c(Cl)c2)c2ccc(Cl)c(Cl)c2)c1O] | WO 2016/109257 Example 1 | White Foam |
| 6 | 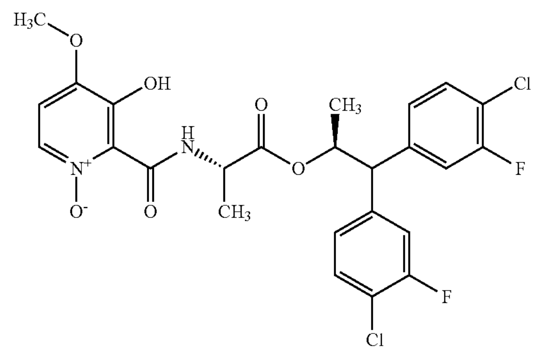 [SMILES: COc1cc[n+]([O-])c(C(=O)N[C@@H](C)C(=O)O[C@@H](C)C(c2ccc(Cl)c(F)c2)c2ccc(Cl)c(F)c2)c1O] | WO 2016/109257 Example 1 | White Foam |
| 7 | 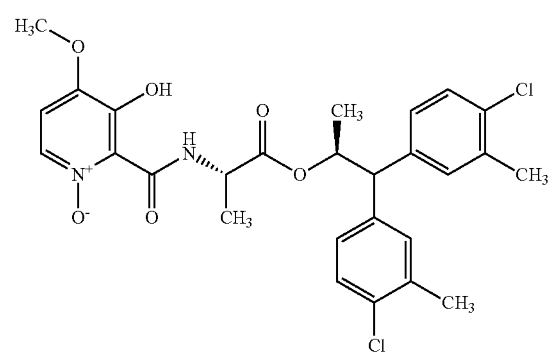 [SMILES: COc1cc[n+]([O-])c(C(=O)N[C@@H](C)C(=O)O[C@@H](C)C(c2ccc(Cl)c(C)c2)c2ccc(Cl)c(C)c2)c1O] | WO 2016/109257 Example 1 | White Foam |
| 8 | 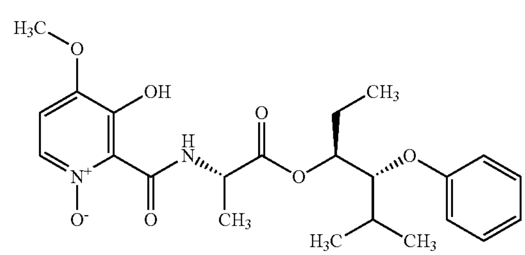 [SMILES: CC[C@H](OC(=O)[C@H](C)NC(=O)c1c(O)c(OC)cc[n+]1[O-])[C@H](Oc1ccccc1)C(C)C] | WO 2016/109289 Example 1 | Thick Oil |

TABLE 1-continued

Compound Structure, Preparation Method, and Appearance

| Cmpd. No. | Structure | As Prepared According To | Appearance |
|---|---|---|---|
| 9 | 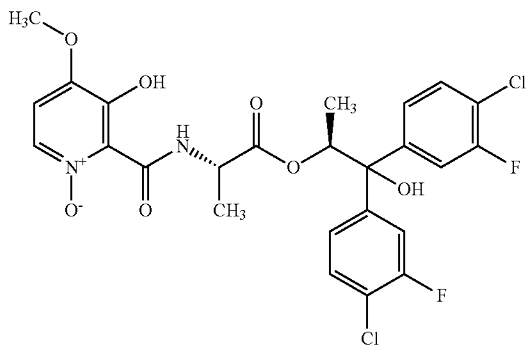 [SMILES: COc1cc[n+]([O-])c(C(=O)N[C@@H](C)C(=O)O[C@@H](C)C(O)(c2ccc(Cl)c(F)c2)c2ccc(Cl)c(F)c2)c1O] | WO 2016/109257 Example 1 | White Foam |
| 10 | 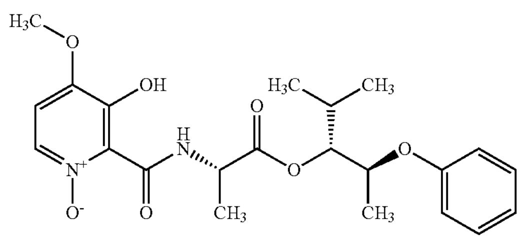 [SMILES: COc1cc[n+]([O-])c(C(=O)N[C@@H](C)C(=O)O[C@H](C(C)C)[C@H](C)Oc2ccccc2)c1O] | WO 2016/109302 Example 1 | Thick Oil |
| 11 | 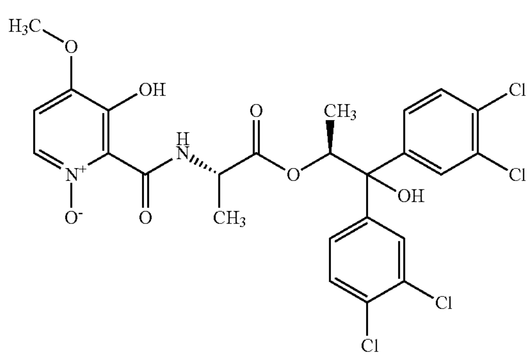 [SMILES: COc1cc[n+]([O-])c(C(=O)N[C@@H](C)C(=O)O[C@@H](C)C(O)(c2ccc(Cl)c(Cl)c2)c2ccc(Cl)c(Cl)c2)c1O] | WO 2016/109257 Example 1 | White Foam |
| 12 | 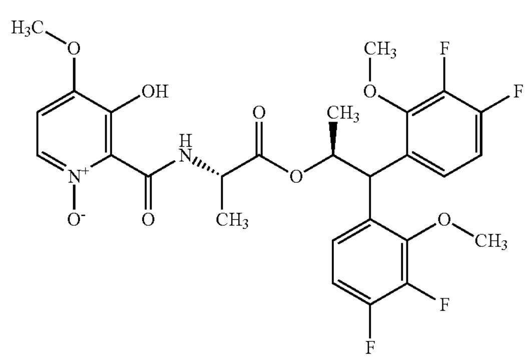 [SMILES: COc1cc[n+]([O-])c(C(=O)N[C@@H](C)C(=O)O[C@@H](C)C(c2ccc(F)c(F)c2OC)c2ccc(F)c(F)c2OC)c1O] | WO 2016/109257 Example 1 | White Foam |

TABLE 1-continued

Compound Structure, Preparation Method, and Appearance

| Cmpd. No. | Structure | As Prepared According To | Appearance |
|---|---|---|---|
| 13 | 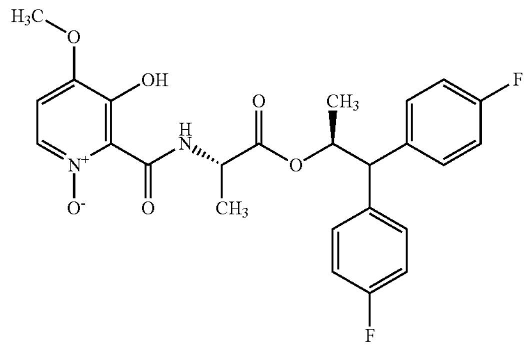 [SMILES: COc1cc[n+]([O-])c(C(=O)N[C@@H](C)C(=O)O[C@@H](C)C(c2ccc(F)cc2)c2ccc(F)cc2)c1O] | WO 2016/109257 Example 1 | Glassy White Solid |
| 14 | 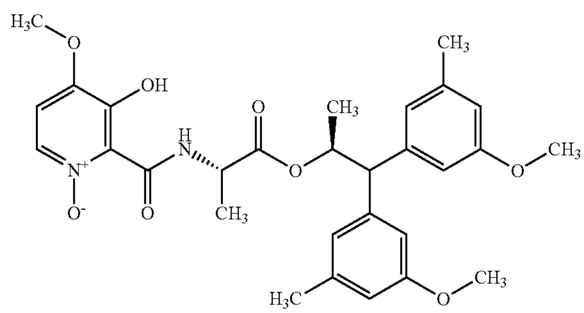 [SMILES: COc1cc(C)cc(C(c2cc(C)cc(OC)c2)[C@H](C)OC(=O)[C@H](C)NC(=O)c2c(O)c(OC)cc[n+]2[O-])c1] | WO 2016/109257 Example 1 | Yellow Semisolid |
| 15 | 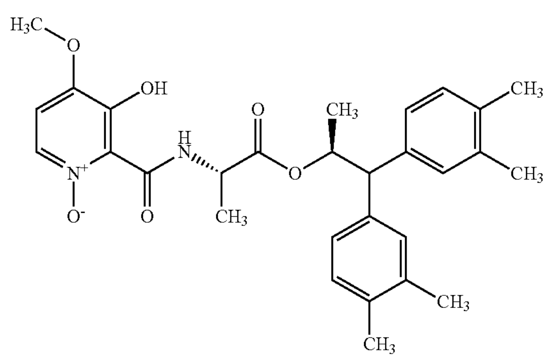 [SMILES: COc1cc[n+]([O-])c(C(=O)N[C@@H](C)C(=O)O[C@@H](C)C(c2ccc(C)c(C)c2)c2ccc(C)c(C)c2)c1O] | WO 2016/109257 Example 1 | White Semisolid |
| 16 | 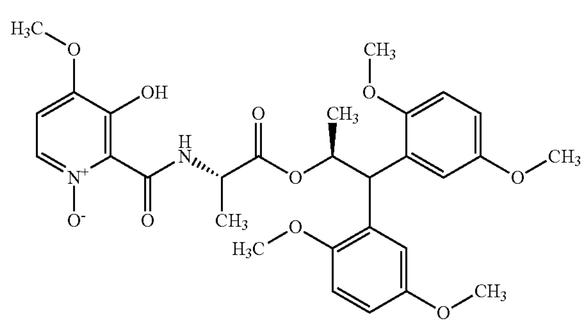 [SMILES: COc1ccc(OC)c(C(c2cc(OC)ccc2OC)[C@H](C)OC(=O)[C@H](C)NC(=O)c2c(O)c(OC)cc[n+]2[O-])c1] | WO 2016/109257 Example 1 | Yellow/Orange Semisolid |

TABLE 1-continued

Compound Structure, Preparation Method, and Appearance

| Cmpd. No. | Structure | As Prepared According To | Appearance |
|---|---|---|---|
| 17 | 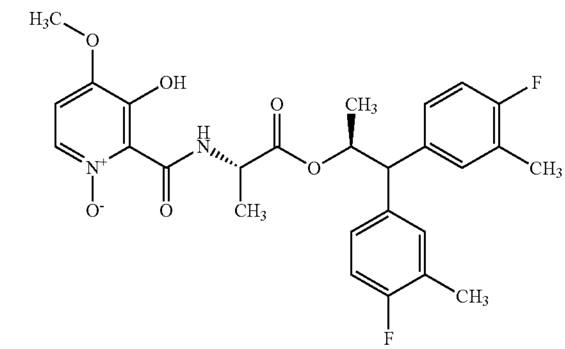 [SMILES: COc1cc[n+]([O-])c(C(=O)N[C@@H](C)C(=O)O[C@@H](C)C(c2ccc(F)c(C)c2)c2ccc(F)c(C)c2)c1O] | WO 2016/109257 Example 1 | White Semisolid |
| 18 | 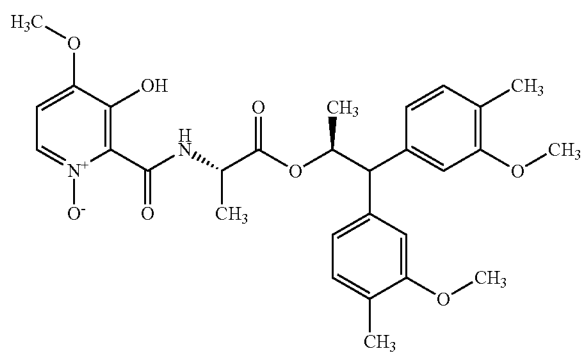 [SMILES: COc1cc(C(c2ccc(C)c(OC)c2)[C@H](C)OC(=O)[C@H](C)NC(=O)c2c(O)c(OC)cc[n+]2[O-])ccc1C] | WO 2016/109257 Example 1 | Yellow Semisolid |
| 19 | 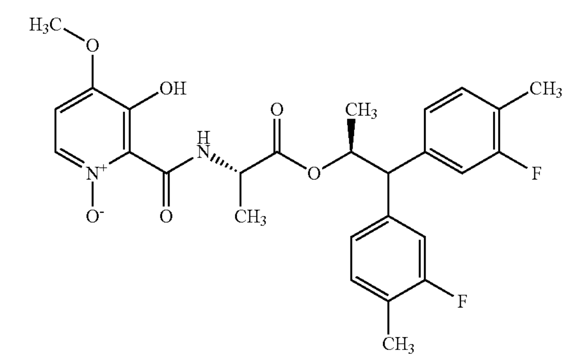 [SMILES: COc1cc[n+]([O-])c(C(=O)N[C@@H](C)C(=O)O[C@@H](C)C(c2ccc(C)c(F)c2)c2ccc(C)c(F)c2)c1O] | WO 2016/109257 Example 1 | Clear, Colorless Oil |
| 20 | 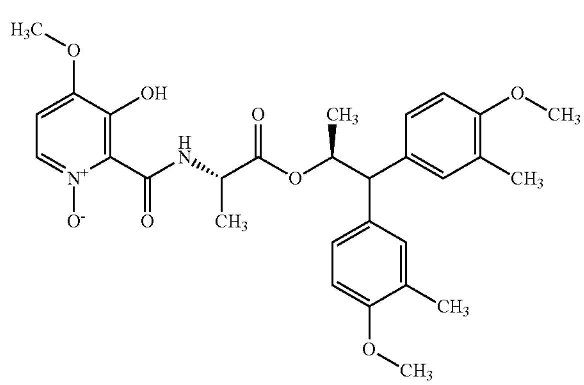 [SMILES: COc1ccc(C(c2ccc(OC)c(C)c2)[C@H](C)OC(=O)[C@H](C)NC(=O)c2c(O)c(OC)cc[n+]2[O-])cc1C] | WO 2016/109257 Example 1 | Pale Yellow Semisolid |

TABLE 1-continued

Compound Structure, Preparation Method, and Appearance

| Cmpd. No. | Structure | As Prepared According To | Appearance |
|---|---|---|---|
| 21 | 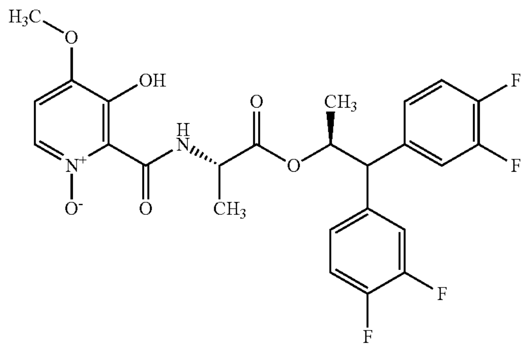 [SMILES: COc1cc[n+]([O-])c(C(=O)N[C@@H](C)C(=O)O[C@@H](C)C(c2ccc(F)c(F)c2)c2ccc(F)c(F)c2)c1O] | WO 2016/109257 Example 1 | White Semisolid |
| 22 | 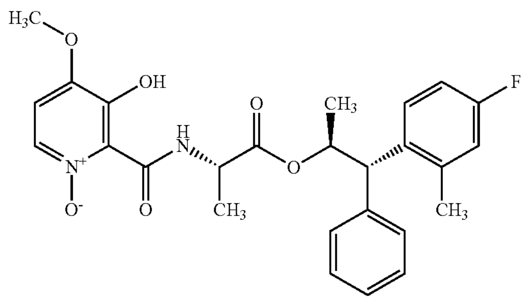 [SMILES: COc1cc[n+]([O-])c(C(=O)N[C@@H](C)C(=O)O[C@@H](C)[C@@H](c2ccccc2)c2ccc(F)cc2C)c1O] | WO 2016/109257 Example 1 | Colorless Oil |
| 23 | 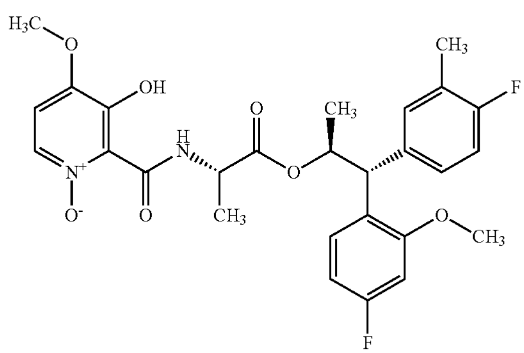 [SMILES: COc1cc(F)ccc1[C@@H](c1ccc(F)c(C)c1)[C@H](C)OC(=O)[C@H](C)NC(=O)c1c(O)c(OC)cc[n+]1[O-]] | WO 2016/109257 Example 1 | Colorless Oil |
| 24 | 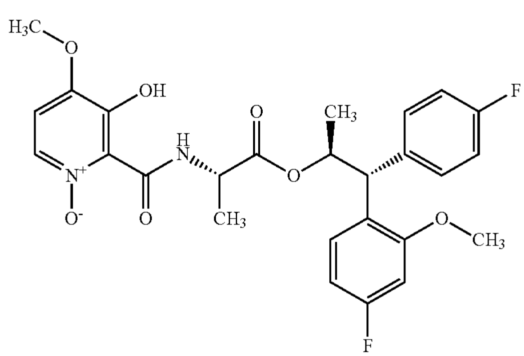 [SMILES: COc1cc(F)ccc1[C@@H](c1ccc(F)cc1)[C@H](C)OC(=O)[C@H](C)NC(=O)c1c(O)c(OC)cc[n+]1[O-]] | WO 2016/109257 Example 1 | Colorless Oil |

TABLE 1-continued

Compound Structure, Preparation Method, and Appearance

| Cmpd. No. | Structure | As Prepared According To | Appearance |
|---|---|---|---|
| 25 | (structure) | WO 2016/109257 Example 1 | Colorless Oil |
| 26 | (structure) | WO 2016/109257 Example 1 | White Wax |
| 27 | (structure) | WO 2016/109257 Example 1 | Colorless Oil |
| 28 | (structure) | WO 2016/109257 Example 1 | White Wax |

TABLE 1-continued

Compound Structure, Preparation Method, and Appearance

| Cmpd. No. | Structure | As Prepared According To | Appearance |
|---|---|---|---|
| 29 | 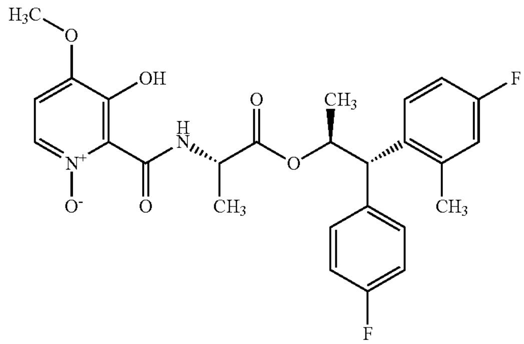 [SMILES: COc1cc[n+]([O-])c(C(=O)N[C@@H](C)C(=O)O[C@@H](C)[C@@H](c2ccc(F)cc2)c2ccc(F)cc2C)c1O] | WO 2016/109257 Example 1 | Colorless Oil |
| 30 | 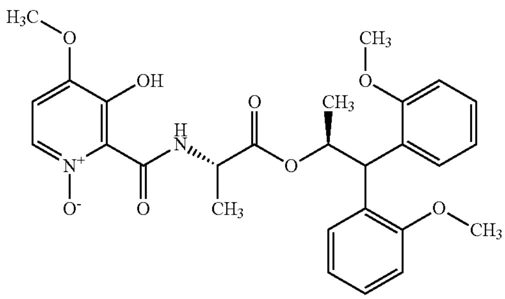 [SMILES: COc1ccccc1C(c1ccccc1OC)[C@H](C)OC(=O)[C@H](C)NC(=O)c1c(O)c(OC)cc[n+]1[O-]] | WO 2016/109257 Example 1 | Colorless Oil |
| 31 | 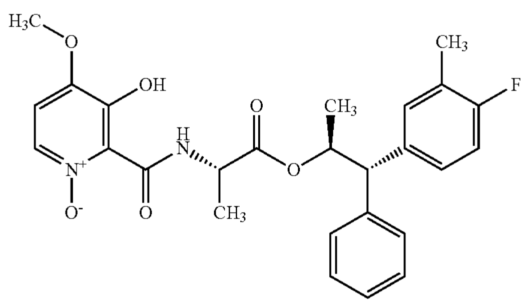 [SMILES: COc1cc[n+]([O-])c(C(=O)N[C@@H](C)C(=O)O[C@@H](C)[C@@H](c2ccccc2)c2ccc(F)c(C)c2)c1O] | WO 2016/109257 Example 1 | Colorless Oil |
| 32 | 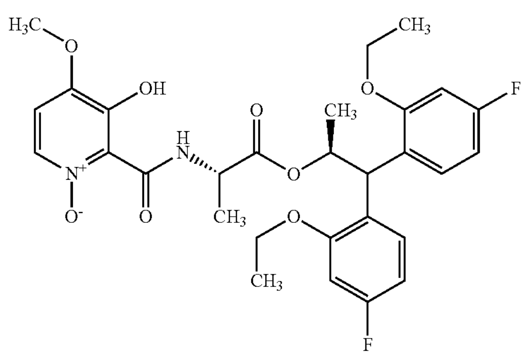 [SMILES: CCOc1cc(F)ccc1C(c1ccc(F)cc1OCC)[C@H](C)OC(=O)[C@H](C)NC(=O)c1c(O)c(OC)cc[n+]1[O-]] | WO 2016/109257 Example 1 | Thick Oil |

TABLE 1-continued

Compound Structure, Preparation Method, and Appearance

| Cmpd. No. | Structure | As Prepared According To | Appearance |
|---|---|---|---|
| 33 | 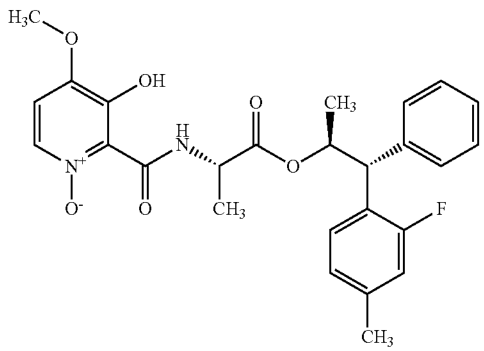 [SMILES: COc1cc[n+]([O-])c(C(=O)N[C@@H](C)C(=O)O[C@@H](C)[C@H](c2ccccc2)c2ccc(C)cc2F)c1O] | WO 2016/109257 Example 1 | White Foam |
| 34 | 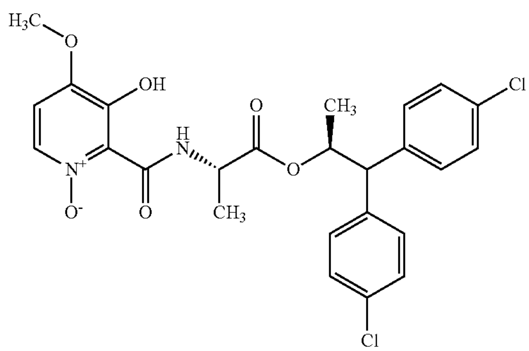 [SMILES: COc1cc[n+]([O-])c(C(=O)N[C@@H](C)C(=O)O[C@@H](C)C(c2ccc(Cl)cc2)c2ccc(Cl)cc2)c1O] | WO 2016/109257 Example 1 | White Foam |
| 35 | 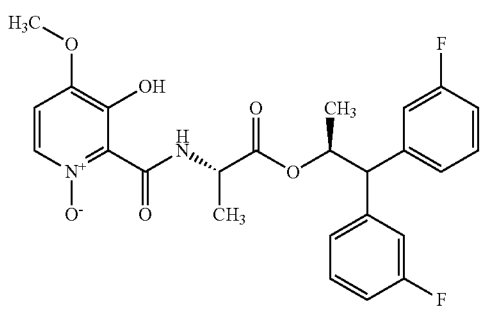 [SMILES: COc1cc[n+]([O-])c(C(=O)N[C@@H](C)C(=O)O[C@@H](C)C(c2cccc(F)c2)c2cccc(F)c2)c1O] | WO 2016/109257 Example 1 | White Foam |
| 36 | 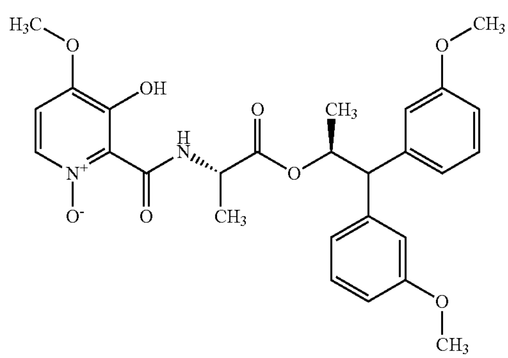 [SMILES: COc1cccc(C(c2cccc(OC)c2)[C@H](C)OC(=O)[C@H](C)NC(=O)c2c(O)c(OC)cc[n+]2[O-])c1] | WO 2016/109257 Example 1 | White Foam |

TABLE 1-continued

Compound Structure, Preparation Method, and Appearance

| Cmpd. No. | Structure | As Prepared According To | Appearance |
|---|---|---|---|
| 37 | 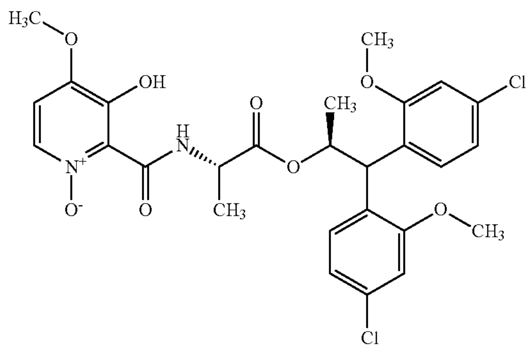 [SMILES: COc1cc(Cl)ccc1C(c1ccc(Cl)cc1OC)[C@H](C)OC(=O)[C@H](C)NC(=O)c1c(O)c(OC)cc[n+]1[O-]] | WO 2016/109257 Example 1 | White Foam |
| 38 | 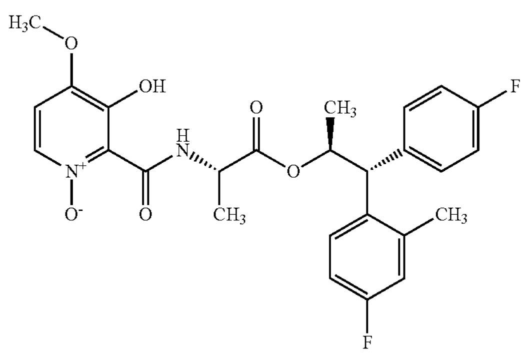 [SMILES: COc1cc[n+]([O-])c(C(=O)N[C@@H](C)C(=O)O[C@@H](C)[C@H](c2ccc(F)cc2)c2ccc(F)cc2C)c1O] | WO 2016/109257 Example 1 | White Foam |
| 39 | 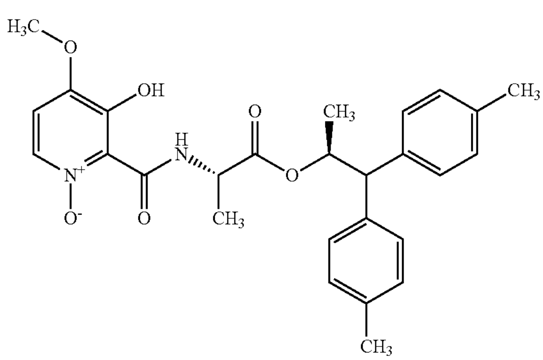 [SMILES: COc1cc[n+]([O-])c(C(=O)N[C@@H](C)C(=O)O[C@@H](C)C(c2ccc(C)cc2)c2ccc(C)cc2)c1O] | WO 2016/109257 Example 1 | White Foam |
| 40 | 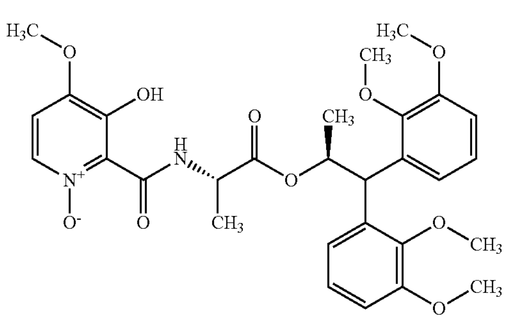 [SMILES: COc1cc[n+]([O-])c(C(=O)N[C@@H](C)C(=O)O[C@@H](C)C(c2cccc(OC)c2OC)c2cccc(OC)c2OC)c1O] | WO 2016/109257 Example 1 | Thick Oil |

TABLE 1-continued

Compound Structure, Preparation Method, and Appearance

| Cmpd. No. | Structure | As Prepared According To | Appearance |
|---|---|---|---|
| 41 | 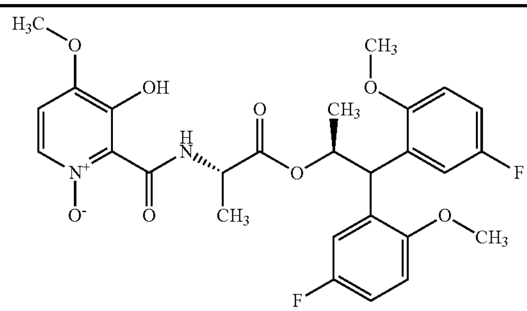 | WO 2016/109257 Example 1 | Thick Oil |

*Cmpd. No.—Compound Number

TABLE 2

Analytical Data

| Cmpd. No. | IR (cm$^{-1}$) | MASS SPEC | NMR |
|---|---|---|---|
| 1 | IR (thin film) 2934, 1736, 1644, 1569, 1533, 1480, 1454, 1301, 1207, 1155, 1030, 911, 808, 733 cm$^{-1}$ | ESIMS m/z 507.2 ([M + H]$^+$) | $^1$H NMR (500 MHz, CDCl$_3$) δ 14.31 (s, 1H), 12.64 (d, J = 7.0 Hz, 1H), 7.85 (d, J = 7.2 Hz, 1H), 7.17 (d, J = 7.9 Hz, 1H), 7.11 (d, J = 7.7 Hz, 1H), 6.98-6.88 (m, 3H), 6.80 (s, 1H), 6.75 (d, J = 7.1 Hz, 1H), 5.67 (dq, J = 10.2, 6.1 Hz, 1H), 4.52-4.38 (m, 2H), 3.96 (s, 3H), 2.35 (s, 3H), 2.28 (s, 3H), 2.24 (s, 3H), 2.20 (s, 3H), 1.30 (d, J = 6.2 Hz, 3H), 1.11 (d, J = 7.2 Hz, 3H). |
| 2 | IR (thin film) 2981, 1737, 1644, 1605, 1570, 1534, 1509, 1479, 1424, 1301, 1220, 1156, 911, 812, 733 cm$^{-1}$ | ESIMS m/z 469.1 ([M + H]$^+$) | $^1$H NMR (500 MHz, CDCl$_3$) δ 14.26 (s, 1H), 12.64 (d, J = 7.1 Hz, 1H), 7.85 (d, J = 7.2 Hz, 1H), 7.29-7.18 (m, 6H), 7.16-7.08 (m, 1H), 6.96 (t, J = 8.7 Hz, 2H), 6.76 (d, J = 7.1 Hz, 1H), 5.76 (dq, J = 10.0, 6.2 Hz, 1H), 4.48 (p, J = 7.2 Hz, 1H), 4.05 (d, J = 10.0 Hz, 1H), 3.97 (s, 3H), 1.25 (d, J = 6.2 Hz, 3H), 1.05 (d, J = 7.2 Hz, 3H). |
| 3 | IR (thin film) 2938, 1738, 1623, 1570, 1533, 1506, 1480, 1456, 1299, 1154, 1030, 911, 734 cm$^{-1}$ | ESIMS m/z 547.1 ([M + H]$^+$) | $^1$H NMR (500 MHz, CDCl$_3$) δ 14.28 (s, 1H), 12.66 (d, J = 7.1 Hz, 1H), 7.85 (d, J = 7.2 Hz, 1H), 7.31-7.23 (m, 1H), 7.16 (t, J = 8.5 Hz, 1H), 6.75 (d, J = 7.2 Hz, 1H), 6.64-6.54 (m, 3H), 6.47 (dd, J = 12.1, 2.6 Hz, 1H), 5.77 (dq, J = 12.2, 6.2 Hz, 1H), 4.62 (d, J = 10.3 Hz, 1H), 4.54 (p, J = 7.2 Hz, 1H), 3.97 (s, 3H), 3.75 (s, 3H), 3.73 (s, 3H), 1.28 (d, J = 6.1 Hz, 3H), 1.18 (d, J = 7.3 Hz, 3H). |
| 4 | IR (thin film) 2938, 1739, 1644, 1570, 1534, 1497, 1424, 1208, 1153, 1032, 911, 809, 732 cm$^{-1}$ | ESIMS m/z 547.1 ([M + H]$^+$) | $^1$H NMR (500 MHz, CDCl$_3$) δ 14.26 (s, 1H), 12.67 (d, J = 7.1 Hz, 1H), 7.85 (d, J = 7.2 Hz, 1H), 6.98-6.90 (m, 2H), 6.88-6.79 (m, 2H), 6.76 (d, J = 7.2 Hz, 1H), 6.70 (dt, J = 9.0, 3.5 Hz, 1H), 6.65-6.59 (m, 1H), 5.84 (dq, J = 12.0, 6.1 Hz, 1H), 4.69 (d, J = 10.4 Hz, 1H), 4.53 (p, J = 7.2 Hz, 1H), 3.97 (s, 3H), 3.74 (s, 6H), 1.31 (d, J = 6.1 Hz, 3H), 1.15 (d, J = 7.2 Hz, 3H). |
| 5 | IR (thin film) 2937, 1739, 1643, 1570, 1533, 1473, 1424, 1302, 1205, 1154, 1133, 1029, 910, 732 cm$^{-1}$ | ESIMS m/z 588.9 ([M + H]$^+$) | $^1$H NMR (500 MHz, CDCl$_3$) δ 14.15 (s, 1H), 12.70 (d, J = 7.0 Hz, 1H), 7.85 (d, J = 7.2 Hz, 1H), 7.42-7.28 (m, 4H), 7.10 (dd, J = 8.4, 2.2 Hz, 1H), 7.06 (dd, J = 8.4, 2.1 Hz, 1H), 6.77 (d, J = 7.2 Hz, 1H), 5.64 (dq, J = 9.6, 6.2 Hz, 1H), 4.53 (p, J = 7.2 Hz, 1H), 4.00 (d, J = 9.5 Hz, 1H), 3.97 (s, 3H), 1.27-1.20 (m, 6H). |

TABLE 2-continued

Analytical Data

| Cmpd. No. | IR (cm$^{-1}$) | MASS SPEC | NMR |
|---|---|---|---|
| 6 | IR (thin film) 2939, 1739, 1644, 1572, 1533, 1484, 1424, 1301, 1244, 1205, 1155, 1062, 910, 733 cm$^{-1}$ | ESIMS m/z 555.0 ([M + H]$^+$) | $^1$H NMR (500 MHz, CDCl$_3$) δ 14.14 (s, 1H), 12.71 (d, J = 7.0 Hz, 1H), 7.86 (d, J = 7.2 Hz, 1H), 7.35-7.27 (m, 2H), 7.07-6.93 (m, 4H), 6.77 (d, J = 7.2 Hz, 1H), 5.65 (dq, J = 9.4, 6.1 Hz, 1H), 4.53 (p, J = 7.1 Hz, 1H), 4.03 (d, J = 9.4 Hz, 1H), 3.97 (s, 3H), 1.26 (d, J = 6.2 Hz, 3H), 1.24 (d, J = 7.2 Hz, 3H). |
| 7 | IR (thin film) 2981, 1737, 1643, 1570, 1533, 1479, 1424, 1301, 1205, 1154, 1047, 910, 732 cm$^{-1}$ | ESIMS m/z 547.0 ([M + H]$^+$) | $^1$H NMR (500 MHz, CDCl$_3$) δ 14.23 (d, J = 0.5 Hz, 1H), 12.65 (d, J = 7.0 Hz, 1H), 7.84 (d, J = 7.2 Hz, 1H), 7.24 (d, J = 8.2 Hz, 1H), 7.16 (d, J = 8.2 Hz, 1H), 7.08 (dd, J = 7.5, 2.2 Hz, 2H), 7.06-6.96 (m, 2H), 6.76 (d, J = 7.2 Hz, 1H), 5.69 (dq, J = 9.9, 6.1 Hz, 1H), 4.50 (p, J = 7.2 Hz, 1H), 3.97 (s, 3H), 3.95 (d, J = 10.1 Hz, 1H), 2.32 (s, 3H), 2.28 (s, 3H), 1.24 (d, J = 6.1 Hz, 3H), 1.14 (d, J = 7.3 Hz, 3H). |
| 8 | IR (thin film) 2968, 1739, 1645, 1595, 1570, 1539, 1488, 1303, 1239, 1205, 1157, 910, 756, 736 cm$^{-1}$ | ESIMS m/z 447.1 ([M + H]$^+$) | $^1$H NMR (500 MHz, CDCl$_3$) δ 14.32 (s, 1H), 12.74 (d, J = 7.1 Hz, 1H), 7.85 (d, J = 7.2 Hz, 1H), 7.20 (dd, J = 8.7, 7.3 Hz, 2H), 6.93-6.83 (m, 3H), 6.75 (d, J = 7.2 Hz, 1H), 5.11 (dt, J = 9.4, 3.8 Hz, 1H), 4.56 (p, J = 7.1 Hz, 1H), 4.24 (dd, J = 6.7, 4.4 Hz, 1H), 3.96 (s, 3H), 1.98 (dt, J = 13.5, 6.8 Hz, 1H), 1.88-1.71 (m, 2H), 1.28 (d, J = 7.2 Hz, 3H), 1.03 (d, J = 6.7 Hz, 3H), 1.01 (d, J = 6.9 Hz, 3H), 0.93 (t, J = 7.4 Hz, 3H). |
| 9 | IR (thin film) 1742, 1654, 1575, 1484, 1422, 1304, 1242, 1157, 1059, 911, 734 cm$^{-1}$ | ESIMS m/z 571.0 ([M + H]$^+$) | $^1$H NMR (500 MHz, CDCl$_3$) δ 13.63 (s, 1H), 12.49 (d, J = 9.2 Hz, 1H), 7.83 (d, J = 7.2 Hz, 1H), 7.32-7.26 (m, 2H), 7.17 (dd, J = 8.4, 7.6 Hz, 1H), 7.04-6.97 (m, 2H), 6.93 (dd, J = 8.4, 2.2 Hz, 1H), 6.76 (d, J = 7.2 Hz, 1H), 5.69 (q, J = 6.3 Hz, 1H), 4.91 (s, 1H), 4.76 (dq, J = 9.3, 7.3 Hz, 1H), 4.00 (s, 3H), 1.48 (d, J = 7.3 Hz, 3H), 1.17 (d, J = 6.2 Hz, 3H). |
| 10 | IR (thin film) 2965, 1744, 1644, 1570, 1532, 1481, 1424, 1302, 1240, 1203, 1154, 1028, 944, 911, 755, 736 cm$^{-1}$ | ESIMS m/z 433.1 ([M + H]$^+$) | $^1$H NMR (500 MHz, CDCl$_3$) δ 14.38 (d, J = 0.5 Hz, 1H), 12.85 (d, J = 6.9 Hz, 1H), 7.87 (d, J = 7.2 Hz, 1H), 7.29-7.23 (m, 2H), 6.98-6.91 (m, 1H), 6.87 (dt, J = 7.9, 1.0 Hz, 2H), 6.77 (d, J = 7.2 Hz, 1H), 5.07 (dd, J = 6.3, 5.3 Hz, 1H), 4.76 (p, J = 7.2 Hz, 1H), 4.51 (p, J = 6.1 Hz, 1H), 3.97 (s, 3H), 2.19-2.09 (m, 1H), 1.63 (d, J = 7.2 Hz, 3H), 1.31 (d, J = 6.2 Hz, 3H), 0.97 (d, J = 6.9 Hz, 3H), 0.91 (d, J = 6.7 Hz, 3H). |
| 11 | IR (thin film) 2986, 1741, 1645, 1574, 1465, 1304, 1251, 1158, 1028, 910, 813, 732 cm$^{-1}$ | ESIMS m/z 604.9 ([M + H]$^+$) | $^1$H NMR (500 MHz, CDCl$_3$) δ 13.60 (s, 1H), 12.47 (d, J = 9.2 Hz, 1H), 7.81 (d, J = 7.1 Hz, 1H), 7.55 (d, J = 2.1 Hz, 1H), 7.33 (d, J = 8.5 Hz, 1H), 7.29 (d, J = 2.2 Hz, 1H), 7.21 (d, J = 8.3 Hz, 1H), 7.10 (dd, J = 8.4, 2.1 Hz, 1H), 7.01 (dd, J = 8.5, 2.2 Hz, 1H), 6.77 (d, J = 7.2 Hz, 1H), 5.67 (q, J = 6.2 Hz, 1H), 4.97 (s, 1H), 4.78 (dq, J = 9.3, 7.3 Hz, 1H), 4.00 (s, 3H), 1.49 (d, J = 7.3 Hz, 3H), 1.17 (d, J = 6.2 Hz, 3H). |
| 12 | IR (thin film) 2941, 1737, 1644, 1570, 1535, 1500, 1475, 1428, 1294, 1027, 1154, 1057, 950, 911, 808, 732 cm$^{-1}$ | ESIMS m/z 583.1 ([M + H]$^+$) | $^1$H NMR (500 MHz, CDCl$_3$) δ 14.21 (s, 1H), 12.66 (d, J = 7.0 Hz, 1H), 7.83 (d, J = 7.2 Hz, 1H), 7.06 (ddd, J = 8.3, 5.3, 2.1 Hz, 1H), 6.87-6.71 (m, 4H), 5.65 (dq, J = 8.4, 6.2 Hz, 1H), 4.85 (d, J = 9.8 Hz, 1H), 4.58-4.48 (m, 1H), 4.00-3.95 (m, 6H), 3.84 (d, J = 2.0 Hz, 3H), 1.25 (d, J = 5.3 Hz, 3H), 1.24 (d, J = 4.2 Hz, 3H). |
| 13 | IR (thin film) 2983, 1737, 1643, | ESIMS m/z 487.1 ([M + H]$^+$) | $^1$H NMR (500 MHz, CDCl$_3$) δ 14.22 (s, 1H), 12.65 (d, J = 7.0 Hz, 1H), 7.85 (d, J = 7.1 Hz, 1H), 7.26-7.16 (m, 4H), 6.97 |

TABLE 2-continued

Analytical Data

| Cmpd. No. | IR (cm$^{-1}$) | MASS SPEC | NMR |
|---|---|---|---|
| | 1570, 1507, 1479, 1453, 1301, 1221, 1157, 1137, 1029, 908, 824, 729, 673 cm$^{-1}$ | | (t, J = 8.7 Hz, 2H), 6.91 (t, J = 8.7 Hz, 2H), 6.76 (d, J = 7.2 Hz, 1H), 5.70 (dq, J = 9.8, 6.1 Hz, 1H), 4.50 (p, J = 7.1 Hz, 1H), 4.05 (d, J = 9.8 Hz, 1H), 3.97 (s, 3H), 1.24 (d, J = 6.2 Hz, 3H), 1.14 (d, J = 7.2 Hz, 3H). $^{13}$C NMR (126 MHz, CDCl$_3$) δ 170.97, 165.41, 162.70, 162.53, 160.74, 160.57, 152.49, 149.36, 136.93, 136.90, 136.80, 136.77, 130.86, 129.53, 129.50, 129.47, 129.44, 123.60, 115.78, 115.61, 115.37, 115.20, 107.63, 73.21, 56.53, 56.09, 48.66, 19.04, 17.14. |
| 14 | IR (thin film) 2936, 1738, 1595, 1573, 1481, 1296, 1154, 1067, 736 cm$^{-1}$ | HRMS-ESI (m/z) [M + H]$^+$ calcd for C$_{29}$H$_{35}$N$_2$O$_8$, 539.2388; found, 539.2409 | $^1$H NMR (400 MHz, CDCl$_3$) δ 14.30 (s, 1H), 12.62 (d, J = 7.2 Hz, 1H), 7.85 (d, J = 7.0 Hz, 1H), 6.75 (d, J = 7.2 Hz, 1H), 6.72-6.57 (m, 5H), 6.57-6.40 (m, 2H), 5.79-5.68 (m, 1H), 4.49 (t, J = 7.1 Hz, 1H), 3.96 (s, 3H), 3.75 (s, 3H), 3.72 (s, 3H), 2.28 (s, 3H), 2.23 (s, 3H), 1.36-1.18 (m, 3H), 1.07 (d, J = 7.2 Hz, 3H). |
| 15 | IR (thin film) 2937, 1737, 1571, 1481, 1302, 1209, 1029, 733 cm$^{-1}$ | HRMS-ESI (m/z) [M + H]$^+$ calcd for C$_{29}$H$_{35}$N$_2$O$_6$, 507.2490; found, 507.2519 | $^1$H NMR (400 MHz, CDCl$_3$) δ 14.32 (s, 1H), 12.60 (d, J = 7.1 Hz, 1H), 7.91-7.81 (m, 1H), 7.01 (q, J = 4.8, 4.1 Hz, 5H), 6.93 (d, J = 8.2 Hz, 1H), 6.75 (d, J = 7.3 Hz, 1H), 5.75 (dq, J = 10.2, 6.1 Hz, 1H), 4.48 (p, J = 7.1 Hz, 1H), 3.96 (s, 3H), 3.91 (d, J = 10.4 Hz, 1H), 2.20 (s, 3H), 2.17 (s, 3H), 2.15 (s, 3H), 2.13 (s, 3H), 1.24 (d, J = 6.1 Hz, 3H), 1.05 (d, J = 7.2 Hz, 3H). $^{13}$C NMR (101 MHz, CDCl$_3$) δ 171.08, 165.31, 152.56, 149.28, 139.27, 139.09, 136.80, 136.33, 134.95, 134.50, 130.87, 129.91, 129.54, 129.36, 129.24, 125.32, 125.07, 123.79, 107.61, 73.64, 57.13, 56.50, 48.64, 19.86, 19.76, 19.28, 19.24, 19.20, 17.15. |
| 16 | IR (thin film) 2942, 1738, 1499, 1224, 1048, 735 cm$^{-1}$ | HRMS-ESI (m/z) [M + H]$^+$ calcd for C$_{29}$H$_{35}$N$_2$O$_{10}$, 571.2286; found, 571.2322 | $^1$H NMR (400 MHz, CDCl$_3$) δ 14.34 (s, 1H), 12.59 (d, J = 7.1 Hz, 1H), 7.85 (dd, J = 7.2, 3.2 Hz, 1H), 7.04 (d, J = 3.0 Hz, 1H), 6.89 (s, 1H), 6.81-6.72 (m, 2H), 6.71-6.64 (m, 2H), 6.61 (dd, J = 8.8, 3.0 Hz, 1H), 5.94 (dq, J = 10.3, 6.1 Hz, 1H), 4.91 (d, J = 10.1 Hz, 1H), 4.50 (p, J = 7.0 Hz, 1H), 3.96 (d, J = 3.4 Hz, 3H), 3.81 (s, 3H), 3.73 (s, 3H), 3.71 (s, 6H), 1.25 (d, J = 6.7 Hz, 3H), 1.09 (d, J = 7.2 Hz, 3H). |
| 17 | IR (thin film) 2933, 1737, 1533, 1501, 1239, 1118, 731 cm$^{-1}$ | HRMS-ESI (m/z) [M + H]$^+$ calcd for C$_{27}$H$_{29}$F$_2$N$_2$O$_6$, 515.1988; found, 515.2023 | $^1$H NMR (400 MHz, CDCl$_3$) δ 14.25 (s, 1H), 12.63 (d, J = 7.0 Hz, 1H), 7.86 (d, J = 7.1 Hz, 1H), 7.04 (td, J = 6.9, 3.7 Hz, 4H), 6.90 (dd, J = 10.2, 7.8 Hz, 1H), 6.87-6.80 (m, 1H), 6.76 (d, J = 7.2 Hz, 1H), 5.67 (dq, J = 10.0, 6.0 Hz, 1H), 4.49 (p, J = 7.2 Hz, 1H), 3.97 (s, 3H), 3.94 (d, J = 10.4 Hz, 1H), 2.23 (d, J = 1.9 Hz, 3H), 2.20-2.17 (m, 3H), 1.23 (d, J = 6.1 Hz, 3H), 1.12 (d, J = 7.2 Hz, 3H). $^{19}$F NMR (376 MHz, CDCl$_3$) δ -119.99, -120.53. |
| 18 | IR (thin film) 2935, 1736, 1572, 1455, 1208, 1154, 1137, 1035, 732 cm$^{-1}$ | HRMS-ESI (m/z) [M + H]$^+$ calcd for C$_{29}$H$_{35}$N$_2$O$_8$, 539.2388; found, 539.2419 | $^1$H NMR (400 MHz, CDCl$_3$) δ 14.28 (s, 1H), 12.61 (d, J = 7.1 Hz, 1H), 7.85 (d, J = 7.2 Hz, 1H), 7.02 (d, J = 7.7 Hz, 1H), 6.94 (d, J = 7.6 Hz, 1H), 6.81-6.66 (m, 6H), 5.79 (dq, J = 12.3, 6.1 Hz, 1H), 4.49 (p, J = 7.1 Hz, 1H), 3.96 (s, 3H), 3.79 (s, 3H), 3.77 (s, 3H), 2.13 (s, 3H), 2.09 (s, 3H), 1.26 (t, J = 3.1 Hz, 3H), 1.07 (d, J = 7.2 Hz, 3H). $^{13}$C NMR (101 MHz, CDCl$_3$) δ 171.14, 165.33, 157.85, 157.61, 152.56, 149.31, 140.43, 140.23, 130.83, 130.75, 130.42, 125.21, 124.75, 119.76, 119.54, 109.77, 109.73, 107.62, 73.39, 57.91, 56.50, |

TABLE 2-continued

Analytical Data

| Cmpd. No. | IR (cm$^{-1}$) | MASS SPEC | NMR |
|---|---|---|---|
| | | | 55.29, 55.25, 48.69, 29.30, 19.22, 17.16, 15.80, 15.70. |
| 19 | IR (thin film) 2933, 1737, 1571, 1506, 1423, 1206, 1155, 733 cm$^{-1}$ | HRMS-ESI (m/z) [M + H]$^+$ calcd for C$_{27}$H$_{29}$F$_2$N$_2$O$_6$, 515.1988; found, 515.1983 | $^1$H NMR (400 MHz, CDCl$_3$) δ 14.23 (s, 1H), 12.65 (d, J = 7.1 Hz, 1H), 7.87 (d, J = 7.2 Hz, 1H), 7.06 (dt, J = 21.0, 7.9 Hz, 2H), 6.99-6.83 (m, 5H), 6.77 (d, J = 7.1 Hz, 1H), 5.68 (dq, J = 9.9, 6.1 Hz, 1H), 4.51 (p, J = 7.2 Hz, 1H), 3.97 (s, 3H), 2.20 (d, J = 1.8 Hz, 3H), 2.16 (d, J = 1.8 Hz, 3H), 1.24 (d, J = 6.1 Hz, 3H), 1.16 (d, J = 7.2 Hz, 3H). $^{19}$F NMR (376 MHz, CDCl$_3$) δ −116.62, −117.26. |
| 20 | IR (thin film) 2935, 1737, 1571, 1504, 1247, 1211, 1031, 734 cm$^{-1}$ | HRMS-ESI (m/z) [M + H]$^+$ calcd for C$_{29}$H$_{35}$N$_2$O$_8$, 539.2388; found, 539.2405 | $^1$H NMR (400 MHz, CDCl$_3$) δ 14.32 (s, 1H), 12.62 (d, J = 7.2 Hz, 1H), 7.85 (d, J = 7.1 Hz, 1H), 7.10-6.98 (m, 4H), 6.79-6.64 (m, 3H), 5.69 (dq, J = 10.4, 6.2 Hz, 1H), 4.49 (h, J = 7.4 Hz, 1H), 3.96 (s, 3H), 3.87 (d, J = 10.3 Hz, 1H), 3.77 (s, 3H), 3.74 (s, 3H), 2.16 (s, 3H), 2.10 (s, 3H), 1.23 (d, J = 6.1 Hz, 3H), 1.08 (d, J = 7.2 Hz, 3H). $^{13}$C NMR (101 MHz, CDCl$_3$) δ 171.12, 165.35, 156.53, 156.28, 152.56, 149.29, 133.74, 133.55, 130.86, 130.52, 130.34, 126.82, 126.31, 126.07, 125.57, 123.77, 110.06, 109.85, 107.61, 77.23, 73.77, 56.49, 56.25, 55.29, 48.69, 19.22, 17.21, 16.33, 16.20. |
| 21 | IR (thin film) 2940, 1738, 1516, 1427, 1284, 1208, 755, 732 cm$^{-1}$ | HRMS-ESI (m/z) [M + H]$^+$ calcd for C$_{25}$H$_{23}$F$_4$N$_2$O$_6$, 523.1487; found, 523.1479 | $^1$H NMR (400 MHz, CDCl$_3$) δ 14.15 (s, 1H), 12.69 (d, J = 7.0 Hz, 1H), 7.87 (d, J = 7.2 Hz, 1H), 7.16-6.91 (m, 6H), 6.78 (d, J = 7.2 Hz, 1H), 5.63 (dq, J = 9.4, 6.2 Hz, 1H), 4.53 (p, J = 7.2 Hz, 1H), 4.00 (d, J = 9.5 Hz, 1H), 3.98 (s, 3H), 1.24 (app t, J = 6.8 Hz, 6H). $^{19}$F NMR (376 MHz, CDCl$_3$) δ −136.29 (d, J = 21.1 Hz), −136.90 (d, J = 21.1 Hz), −139.33 (d, J = 21.2 Hz), −139.70 (d, J = 21.5 Hz). |
| 22 | IR (thin film) 2982, 1738, 1571, 1481, 1453, 1245, 1157 cm$^{-1}$ | HRMS-ESI (m/z) [M + H]$^+$ calcd for C$_{26}$H$_{28}$FN$_2$O$_6$, 483.1926; found, 483.1968 | $^1$H NMR (500 MHz, CDCl$_3$) δ 14.27 (s, 1H), 12.61 (d, J = 7.0 Hz, 1H), 7.86 (d, J = 7.2 Hz, 1H), 7.30 (dd, J = 8.7, 5.7 Hz, 1H), 7.26-7.22 (m, 2H), 7.18 (dd, J = 8.5, 6.9 Hz, 2H), 7.12-7.06 (m, 1H), 6.91-6.81 (m, 2H), 6.76 (d, J = 7.2 Hz, 1H), 5.76 (dq, J = 10.3, 6.1 Hz, 1H), 4.52-4.43 (m, 1H), 4.29 (d, J = 10.4 Hz, 1H), 3.96 (s, 3H), 2.38 (s, 3H), 1.27 (d, J = 6.1 Hz, 3H), 1.05 (d, J = 7.2 Hz, 3H). $^{19}$F NMR (471 MHz, CDCl$_3$) δ −116.71. |
| 23 | IR (thin film) 2939, 1737, 1572, 1502, 1481, 1208, 734 cm$^{-1}$ | HRMS-ESI (m/z) [M + H]$^+$ calcd for C$_{27}$H$_{29}$F$_2$N$_2$O$_7$, 531.1937; found, 531.1984 | $^1$H NMR (500 MHz, CDCl$_3$) δ 14.27 (s, 1H), 12.62 (d, J = 7.0 Hz, 1H), 7.84 (d, J = 7.1 Hz, 1H), 7.23 (dd, J = 8.5, 6.6 Hz, 1H), 7.10-6.99 (m, 2H), 6.87 (t, J = 9.3 Hz, 1H), 6.75 (d, J = 7.2 Hz, 1H), 6.56 (td, J = 8.3, 2.5 Hz, 1H), 6.47 (dd, J = 10.9, 2.5 Hz, 1H), 5.74 (dq, J = 10.3, 6.1 Hz, 1H), 4.54-4.45 (m, 1H), 4.43 (d, J = 10.3 Hz, 1H), 3.96 (s, 3H), 3.77 (s, 3H), 2.21 (d, J = 2.0 Hz, 3H), 1.21 (d, J = 6.1 Hz, 3H), 1.13 (d, J = 7.3 Hz, 3H). $^{19}$F NMR (471 MHz, CDCl$_3$) δ −113.43, −120.41. |
| 24 | | HRMS-ESI (m/z) [M + H]$^+$ calcd for C$_{26}$H$_{27}$F$_2$N$_2$O$_7$, 517.1781; found, 517.1840 | $^1$H NMR (500 MHz, CDCl$_3$) δ 14.25 (s, 1H), 12.62 (d, J = 7.0 Hz, 1H), 7.84 (d, J = 7.1 Hz, 1H), 7.25-7.17 (m, 3H), 6.98-6.90 (m, 2H), 6.75 (d, J = 7.2 Hz, 1H), 6.55 (td, J = 8.3, 2.5 Hz, 1H), 6.47 (dd, J = 10.9, 2.5 Hz, 1H), 5.76 (dq, J = 10.1, 6.2 Hz, 1H), 4.54-4.44 (m, 2H), 3.96 (s, 3H), 3.75 (s, 3H), 1.21 (d, J = 6.2 Hz, 3H), 1.14 (d, J = 7.3 Hz, 3H). $^{19}$F NMR (471 MHz, CDCl$_3$) δ −113.26, −116.12. |
| 25 | IR (thin film) 2981, | HRMS-ESI (m/z) [M + H]$^+$ calcd | $^1$H NMR (500 MHz, CDCl$_3$) δ 14.31 (s, 1H), 12.62 (d, J = 7.0 Hz, 1H), 7.85 (d, J = |

TABLE 2-continued

Analytical Data

| Cmpd. No. | IR (cm$^{-1}$) | MASS SPEC | NMR |
|---|---|---|---|
| | 1736, 1571, 1479, 1453, 1207, 1154, 730 cm$^{-1}$ | for C$_{27}$H$_{31}$N$_2$O$_6$, 479.2177; found, 449.2214 | 7.2 Hz, 1H), 7.20-7.12 (m, 1H), 7.11-7.07 (m, 5H), 7.02-6.97 (m, 1H), 6.94-6.89 (m, 1H), 6.75 (d, J = 7.2 Hz, 1H), 5.78 (dq, J = 10.4, 6.1 Hz, 1H), 4.53-4.42 (m, 1H), 3.98-3.94 (m, 4H), 2.30 (s, 3H), 2.26 (s, 3H), 1.24 (d, J = 6.1 Hz, 3H), 1.03 (d, J = 7.2 Hz, 3H). |
| 26 | IR (thin film) 2935, 1735, 1510, 1244, 1029, 813, 729 cm$^{-1}$ | HRMS-ESI (m/z) [M + H]$^+$ calcd for C$_{27}$H$_{31}$N$_2$O$_8$, 511.2075; found, 511.2128 | $^1$H NMR (500 MHz, CDCl$_3$) δ 14.28 (s, 1H), 12.61 (d, J = 7.1 Hz, 1H), 7.85 (d, J = 7.1 Hz, 1H), 7.20-7.11 (m, 4H), 6.83-6.68 (m, 5H), 5.70 (dq, J = 9.8, 6.1 Hz, 1H), 4.57-4.38 (m, 1H), 3.96 (s, 4H), 3.75 (s, 3H), 3.72 (s, 3H), 1.23 (d, J = 6.2 Hz, 3H), 1.11 (d, J = 7.2 Hz, 3H). |
| 27 | IR (thin film) 2984, 1737, 1571, 1481, 1303, 1223, 1156, 702 cm$^{-1}$ | HRMS-ESI (m/z) [M + H]$^+$ calcd for C$_{26}$H$_{29}$N$_2$O$_6$, 465.2020; found, 465.2064 | $^1$H NMR (500 MHz, CDCl$_3$) δ 14.29 (s, 1H), 12.71 (d, J = 7.1 Hz, 1H), 7.86 (d, J = 7.1 Hz, 1H), 7.34-7.08 (m, 10H), 6.75 (d, J = 7.1 Hz, 1H), 5.86 (q, J = 6.2 Hz, 1H), 4.61-4.52 (m, 1H), 3.96 (s, 3H), 1.74 (s, 3H), 1.21 (d, J = 7.2 Hz, 3H), 1.16 (d, J = 6.3 Hz, 3H). |
| 28 | IR (thin film) 2982, 1737, 1634, 1571, 1480, 1453, 1209, 1155, 730 cm$^{-1}$ | HRMS-ESI (m/z) [M + H]$^+$ calcd for C$_{27}$H$_{30}$FN$_2$O$_6$, 497.2082; found, 497.2118 | $^1$H NMR (500 MHz, CDCl$_3$) δ 14.29 (s, 1H), 12.64 (d, J = 7.1 Hz, 1H), 7.86 (d, J = 7.1 Hz, 1H), 7.22 (t, J = 7.9 Hz, 1H), 7.16 (d, J = 8.1 Hz, 2H), 7.07 (d, J = 7.8 Hz, 2H), 6.86-6.83 (m, 1H), 6.75 (d, J = 7.2 Hz, 1H), 6.74-6.69 (m, 1H), 5.83-5.72 (m, 1H), 4.56-4.48 (m, 1H), 4.37 (d, J = 10.3 Hz, 1H), 3.96 (s, 3H), 2.27 (s, 3H), 2.23 (s, 3H), 1.25 (d, J = 6.1 Hz, 3H), 1.12 (d, J = 7.2 Hz, 3H). $^{19}$F NMR (471 MHz, CDCl$_3$) δ −119.19. |
| 29 | IR (thin film) 2982, 1738, 1571, 1481, 1222, 1158, 735 cm$^{-1}$ | HRMS-ESI (m/z) [M + H]$^+$ calcd for C$_{26}$H$_{27}$F$_2$N$_2$O$_6$, 501.1832; found, 501.1854 | $^1$H NMR (500 MHz, CDCl$_3$) δ 14.23 (d, J = 0.5 Hz, 1H), 12.64 (d, J = 6.9 Hz, 1H), 7.86 (d, J = 7.2 Hz, 1H), 7.26-7.18 (m, 3H), 6.92-6.82 (m, 4H), 6.77 (d, J = 7.2 Hz, 1H), 5.70 (dq, J = 9.9, 6.1 Hz, 1H), 4.54-4.43 (m, 1H), 4.27 (d, J = 10.2 Hz, 1H), 3.97 (s, 3H), 2.35 (s, 3H), 1.27 (d, J = 6.2 Hz, 3H), 1.15 (d, J = 7.2 Hz, 3H). $^{19}$F NMR (471 MHz, CDCl$_3$) δ −116.00, −116.39. |
| 30 | IR (thin film) 2937, 1736, 1571, 1491, 1462, 1245, 1029, 756 cm$^{-1}$ | HRMS-ESI (m/z) [M + H]$^+$ calcd for C$_{27}$H$_{31}$N$_2$O$_8$, 511.2075; found, 511.2116 | $^1$H NMR (500 MHz, CDCl$_3$) δ 14.34 (s, 1H), 12.60 (d, J = 7.1 Hz, 1H), 7.84 (d, J = 7.2 Hz, 1H), 7.44 (dd, J = 7.6, 1.7 Hz, 1H), 7.26-7.23 (m, 1H), 7.15-7.03 (m, 2H), 6.84-6.80 (m, 3H), 6.74 (dd, J = 7.9, 1.5 Hz, 2H), 5.95 (dq, J = 10.0, 6.2 Hz, 1H), 4.98 (dd, J = 9.8, 2.3 Hz, 1H), 4.57-4.46 (m, 1H), 3.95 (s, 3H), 3.83 (s, 3H), 3.74 (s, 3H), 1.24 (d, J = 6.2 Hz, 3H), 1.05 (d, J = 7.3 Hz, 3H). |
| 31 | IR (thin film) 2983, 1737, 1571, 1503, 1453, 1207, 1156 cm$^{-1}$ | HRMS-ESI (m/z) [M + H]$^+$ calcd for C$_{26}$H$_{28}$N$_2$O$_6$, 483.1926; found, 483.1976 | $^1$H NMR (500 MHz, CDCl$_3$) δ 14.27 (s, 1H), 12.62 (d, J = 7.0 Hz, 1H), 7.85 (d, J = 7.2 Hz, 1H), 7.29-7.02 (m, 7H), 6.94-6.85 (m, 1H), 6.75 (d, J = 7.1 Hz, 1H), 5.75 (dq, J = 10.2, 6.2 Hz, 1H), 4.53-4.42 (m, 1H), 3.99 (d, J = 10.3 Hz, 1H), 3.96 (s, 3H), 2.22 (d, J = 1.9 Hz, 3H), 1.24 (d, J = 6.1 Hz, 3H), 1.03 (d, J = 7.2 Hz, 3H). $^{19}$F NMR (471 MHz, CDCl$_3$) δ −120.17 |
| 32 | IR (thin film) 2981, 1736, 1713, 1644, 1598, 1571, 1535, 1500, 1426, 1221, 1161, 1041, 911, 735 cm$^{-1}$ | | $^1$H NMR (500 MHz, CDCl$_3$) δ 14.31 (s, 1H), 12.64 (d, J = 6.9 Hz, 1H), 7.84 (d, J = 7.1 Hz, 1H), 7.31 (dd, J = 8.6, 6.8 Hz, 1H), 7.20-7.12 (m, 1H), 6.75 (d, J = 7.2 Hz, 1H), 6.55-6.49 (m, 3H), 6.43 (dd, J = 11.0, 2.6 Hz, 1H), 5.95-5.88 (m, 1H), 4.79 (d, J = 10.2 Hz, 1H), 4.50 (p, J = 7.1 Hz, 1H), 4.03-3.89 (m, 7H), 3.85 (dq, J = 9.0, 7.0 Hz, 1H), 1.47 (t, J = 7.0 Hz, 3H), 1.40 (t, J = 6.9 Hz, 3H), 1.23 (d, J = 6.2 Hz, 3H), 1.15 (d, J = 7.3 Hz, 3H). |

TABLE 2-continued

Analytical Data

| Cmpd. No. | IR (cm$^{-1}$) | MASS SPEC | NMR |
|---|---|---|---|
| | | | $^{13}$C NMR (126 MHz, CDCl$_3$) δ 171.12, 165.38, 157.59, 152.50, 149.29, 148.38, 130.82, 107.58, 63.80, 56.51, 48.75, 29.28, 14.62. |
| 33 | IR (thin film) 2981, 1739, 1644, 1571, 1533, 1480, 1453, 1425, 1302, 1208, 1155, 1029, 730 cm$^{-1}$ | HRMS-ESI (m/z) [M + H]$^+$ calcd for C$_{26}$H$_{28}$FN$_2$O$_6$, 483.1926; found, 483.1939 | $^1$H NMR (500 MHz, CDCl$_3$) δ 14.28 (d, J = 0.5 Hz, 1H), 12.67 (d, J = 7.1 Hz, 1H), 7.86 (d, J = 7.1 Hz, 1H), 7.32-7.16 (m, 6H), 6.86 (dd, J = 8.2, 1.5 Hz, 1H), 6.79-6.68 (m, 2H), 5.85-5.73 (m, 1H), 4.53 (p, J = 7.2 Hz, 1H), 4.41 (d, J = 10.2 Hz, 1H), 3.96 (s, 3H), 2.24 (s, 3H), 1.26 (d, J = 6.1 Hz, 3H), 1.12 (d, J = 7.2 Hz, 3H). $^{13}$C NMR (126 MHz, CDCl$_3$) δ 171.01, 165.36, 160.53 (d, J = 245.0 Hz), 152.50, 149.22, 140.36, 130.87, 128.74, 128.30, 126.97, 124.80, 123.73, 115.89 (d, J = 22.6 Hz), 107.58, 72.81, 56.50, 49.19, 48.55, 29.28, 20.83, 19.11, 17.17. |
| 34 | IR (thin film) 2939, 1736, 1642, 1569, 1531, 1479, 1451, 1423, 1298, 1206, 1153, 1066, 1013, 796, 728 cm$^{-1}$ | HRMS-ESI (m/z) [M + H]$^+$ calcd for C$_{25}$H$_{25}$Cl$_2$N$_2$O$_6$, 519.1084; found, 519.1081 | $^1$H NMR (500 MHz, CDCl$_3$) δ 14.21 (s, 1H), 12.66 (d, J = 7.0 Hz, 1H), 7.85 (d, J = 7.2 Hz, 1H), 7.28-7.21 (m, 6H), 7.21-7.13 (m, 2H), 6.76 (d, J = 7.2 Hz, 1H), 5.70 (dq, J = 9.7, 6.2 Hz, 1H), 4.50 (p, J = 7.2 Hz, 1H), 4.03 (d, J = 9.7 Hz, 1H), 3.97 (s, 3H), 1.24 (d, J = 6.2 Hz, 3H), 1.16 (d, J = 7.2 Hz, 3H). $^{13}$C NMR (126 MHz, CDCl$_3$) δ 170.93, 165.42, 152.49, 149.36, 139.34, 139.22, 132.99, 132.67, 130.86, 129.40, 129.02, 128.62, 107.64, 72.82, 56.52, 56.30, 48.64, 19.00, 17.19. |
| 35 | IR (thin film) 2982, 1737, 1643, 1588, 1532, 1481, 1448, 1424, 1301, 1205, 1149, 1028, 950, 755, 728 cm$^{-1}$ | HRMS-ESI (m/z) [M + Na]$^+$ calcd for C$_{25}$H$_{24}$F$_2$N$_2$O$_6$Na, 509.1495; found, 509.1489 | $^1$H NMR (500 MHz, CDCl$_3$) δ 14.21 (d, J = 0.5 Hz, 1H), 12.67 (d, J = 7.1 Hz, 1H), 7.86 (d, J = 7.1 Hz, 1H), 7.26 (s, 2H), 7.10-7.04 (m, 2H), 6.96 (tt, J = 9.8, 2.1 Hz, 2H), 6.93-6.89 (m, 1H), 6.84 (tdd, J = 8.4, 2.6, 0.9 Hz, 1H), 6.76 (d, J = 7.2 Hz, 1H), 5.73 (dq, J = 9.9, 6.2 Hz, 1H), 4.51 (p, J = 7.1 Hz, 1H), 4.05 (d, J = 9.9 Hz, 1H), 3.97 (s, 3H), 1.34-1.22 (m, 3H), 1.14 (d, J = 7.2 Hz, 3H). $^{13}$C NMR (126 MHz, CDCl$_3$) δ 170.90, 165.38, 162.91 (d, J = 246.9 Hz), 162.73 (d, J = 246.3 Hz), 152.50, 149.29, 143.20 (d, J = 7.0 Hz), 142.95 (d, J = 6.8 Hz), 130.92, 130.41 (d, J = 8.3 Hz), 130.08 (d, J = 8.5 Hz), 123.69 (d, J = 3.1 Hz), 123.61, 123.40 (d, J = 2.7 Hz), 115.31 (d, J = 20.7 Hz), 114.16 (d, J = 20.9 Hz), 113.81 (d, J = 20.9 Hz), 107.62, 72.88, 57.06, 56.53, 48.55, 29.28, 19.03, 17.19. |
| 36 | IR (thin film) 2939, 2835, 1736, 1643, 1596, 1570, 1531, 1482, 1451, 1424, 1296, 1206, 1151, 1029, 755, 728 cm$^{-1}$ | HRMS-ESI (m/z) [M + Na]$^+$ calcd for C$_{27}$H$_{30}$N$_2$O$_8$Na, 533.1894; found, 533.1888 | $^1$H NMR (500 MHz, CDCl$_3$) δ 14.28 (s, 1H), 12.63 (d, J = 7.1 Hz, 1H), 7.85 (d, J = 7.2 Hz, 1H), 7.20 (t, J = 8.0 Hz, 1H), 7.13 (t, J = 8.0 Hz, 1H), 6.89 (ddt, J = 7.7, 2.8, 1.2 Hz, 2H), 6.82 (t, J = 2.1 Hz, 2H), 6.78-6.69 (m, 2H), 6.65 (ddd, J = 8.2, 2.6, 0.9 Hz, 1H), 5.78 (dq, J = 10.5, 6.1 Hz, 1H), 4.49 (p, J = 7.2 Hz, 1H), 4.02-3.94 (m, 4H), 3.77 (s, 3H), 3.74 (s, 3H), 1.26 (d, J = 6.1 Hz, 3H), 1.08 (d, J = 7.2 Hz, 3H). $^{13}$C NMR (126 MHz, CDCl$_3$) δ 171.02, 165.32, 159.75, 159.56, 152.52, 149.24, 142.89, 142.61, 130.85, 129.77, 129.40, 123.73, 120.38, 120.08, 114.30, 113.93, 111.85, 107.56, 73.24, 57.91, 56.51, 55.12, 48.60, 19.17, 17.15. |
| 37 | IR (thin film) 2939, 1735, 1643, 1591, 1572, 1487, 1452, | HRMS-ESI (m/z) [M + H]$^+$ calcd for C$_{27}$H$_{29}$Cl$_2$N$_2$O$_8$, 579.1295; found, 579.1298 | $^1$H NMR (500 MHz, CDCl$_3$) δ 14.28 (s, 1H), 12.64 (d, J = 7.0 Hz, 1H), 7.84 (d, J = 7.2 Hz, 1H), 7.31 (d, J = 8.3 Hz, 1H), 7.09 (d, J = 8.2 Hz, 1H), 6.84-6.78 (m, 3H), 6.75 (d, J = 7.2 Hz, 1H), 6.72 (d, J = |

TABLE 2-continued

Analytical Data

| Cmpd. No. | IR (cm$^{-1}$) | MASS SPEC | NMR |
|---|---|---|---|
| | 1301, 1245, 1209, 1150, 1027, 727 cm$^{-1}$ | | 2.0 Hz, 1H), 5.87 (dq, J = 9.6, 6.1 Hz, 1H), 4.81 (d, J = 9.7 Hz, 1H), 4.51 (p, J = 7.2 Hz, 1H), 3.96 (s, 3H), 3.82 (s, 3H), 3.73 (s, 3H), 1.22 (d, J = 6.2 Hz, 3H), 1.16 (d, J = 7.2 Hz, 3H). $^{13}$C NMR (126 MHz, CDCl$_3$) δ 171.03, 165.37, 157.98, 157.84, 152.49, 149.30, 133.15, 132.79, 130.83, 130.43, 129.91, 127.51 (d, J = 3.3 Hz), 123.66, 120.41, 120.02, 111.62, 111.35, 107.60, 72.33, 56.49, 55.70 (d, J = 6.9 Hz), 48.69, 18.75, 17.29. |
| 38 | IR (thin film) 2982, 1736, 1643, 1569, 1532, 1508, 1479, 1423, 1218, 1178, 1154, 805, 727 cm$^{-1}$ | HRMS-ESI (m/z) [M + H]$^+$ calcd for C$_{26}$H$_{27}$F$_2$N$_2$O$_6$, 501.1832; found, 501.1847 | $^1$H NMR (500 MHz, CDCl$_3$) δ 14.22 (d, J = 0.5 Hz, 1H), 12.66 (d, J = 7.1 Hz, 1H), 7.84 (d, J = 7.2 Hz, 1H), 7.30 (dd, J = 8.7, 5.8 Hz, 1H), 7.21-7.12 (m, 3H), 6.96 (t, J = 8.6 Hz, 1H), 6.86 (td, J = 8.5, 3.0 Hz, 1H), 6.76 (d, J = 7.2 Hz, 1H), 6.72 (dd, J = 9.7, 2.8 Hz, 1H), 5.67 (dq, J = 10.0, 6.1 Hz, 1H), 4.49 (p, J = 7.2 Hz, 1H), 4.24 (d, J = 10.0 Hz, 1H), 3.97 (s, 3H), 2.27 (s, 3H), 1.24 (d, J = 6.1 Hz, 3H), 1.14 (d, J = 7.2 Hz, 3H). |
| 39 | IR (thin film) 2980, 2937, 1735, 1642, 1568, 1478, 1450, 1422, 1298, 1206, 1153, 1028, 804, 756, 726 cm$^{-1}$ | HRMS-ESI (m/z) [M + Na]$^+$ calcd for C$_{27}$H$_{30}$N$_2$O$_6$Na, 501.1996; found, 501.1987 | $^1$H NMR (500 MHz, CDCl$_3$) δ 14.30 (s, 1H), 12.63 (d, J = 7.1 Hz, 1H), 7.85 (d, J = 7.2 Hz, 1H), 7.18-7.13 (m, 4H), 7.06 (d, J = 7.8 Hz, 2H), 6.99 (d, J = 7.8 Hz, 2H), 6.75 (d, J = 7.2 Hz, 1H), 5.76 (dq, J = 10.2, 6.1 Hz, 1H), 4.49 (p, J = 7.3 Hz, 1H), 3.98 (d, J = 7.6 Hz, 1H), 3.96 (s, 3H), 2.27 (s, 3H), 2.23 (s, 3H), 1.24 (d, J = 6.1 Hz, 3H), 1.07 (d, J = 7.2 Hz, 3H). $^{13}$C NMR (126 MHz, CDCl$_3$) δ 171.02, 165.31, 152.50, 149.22, 138.69, 138.53, 136.34, 135.99, 130.84, 129.40, 129.02, 127.90, 127.77, 123.77, 107.56, 73.53, 57.04, 56.49, 48.60, 20.96, 20.90, 19.18, 17.15. |
| 40 | IR (thin film) 2939, 1735, 1644, 1571, 1535, 1474, 1425, 1274, 1218, 1154, 1066, 1046, 1003, 726 cm$^{-1}$ | HRMS-ESI (m/z) [M + Na]$^+$ calcd for C$_{29}$H$_{34}$N$_2$O$_{10}$Na, 593.2106; found, 593.2100 | $^1$H NMR (500 MHz, CDCl$_3$) δ 14.35 (s, 1H), 12.63 (d, J = 6.1 Hz, 1H), 7.86-7.79 (m, 1H), 7.06 (dt, J = 8.4, 1.6 Hz, 1H), 7.03-6.97 (m, 1H), 6.91-6.80 (m, 1H), 6.80-6.68 (m, 4H), 5.74-5.61 (m, 1H), 5.16-5.03 (m, 1H), 4.56-4.38 (m, 1H), 3.96 (s, 3H), 3.89 (s, 3H), 3.83 (s, 3H), 3.79 (s, 3H), 3.71 (s, 3H), 1.36 (d, J = 7.2 Hz, 3H), 1.11 (d, J = 7.3 Hz, 3H). |
| 41 | IR (thin film) 2940, 1736, 1643, 1570, 1533, 1493, 1454, 1423, 1243, 1205, 1178, 1152, 1026, 808, 726 cm$^{-1}$ | HRMS-ESI (m/z) [M + Na]$^+$ calcd for C$_{27}$H$_{28}$F$_2$N$_2$O$_8$Na, 569.1706; found, 569.1700 | $^1$H NMR (500 MHz, CDCl$_3$) δ 14.28 (d, J = 0.5 Hz, 1H), 12.66 (d, J = 7.0 Hz, 1H), 7.85 (d, J = 7.1 Hz, 1H), 7.18 (ddd, J = 17.3, 9.7, 3.1 Hz, 1H), 6.97-6.91 (m, 1H), 6.89-6.72 (m, 4H), 6.70 (dt, J = 9.0, 4.6 Hz, 1H), 5.93-5.79 (m, 1H), 4.85 (d, J = 9.5 Hz, 1H), 4.56-4.43 (m, 1H), 3.97 (s, 3H), 3.82 (s, 3H), 3.73 (s, 3H), 1.30-1.22 (m, 3H), 1.17 (d, J = 7.2 Hz, 3H). |

TABLE 3

Biological Testing Rating Scale
Rating Table for Fungal Pathogens

| % Control | Rating |
|---|---|
| >80 | A |
| ≤80 | B |
| Not Tested | C |
| No Activity Observed in the Reported Assay | D |

TABLE 4

Biological Activity - PUCCRT and SEPTTR Disease
Control in High and Low Volume Applications

| | HV activity at 100 ppm | | | | LV activity at 121.5 g/H | | | |
|---|---|---|---|---|---|---|---|---|
| | PUCCRT* | | SEPTTR* | | PUCCRT* | | SEPTTR* | |
| Cmpd. No. | 1DP* | 3DC* | 1DP* | 3DC* | 1DP* | 3DC* | 1DP* | 3DC* |
| 1 | A | B | A | A | A | B | A | A |
| 2 | A | A | A | A | A | A | A | D |

TABLE 4-continued

Biological Activity - PUCCRT and SEPTTR Disease Control in High and Low Volume Applications

| | HV activity at 100 ppm | | | | LV activity at 121.5 g/H | | | |
|---|---|---|---|---|---|---|---|---|
| | PUCCRT* | | SEPTTR* | | PUCCRT* | | SEPTTR* | |
| Cmpd. No. | 1DP* | 3DC* | 1DP* | 3DC* | 1DP* | 3DC* | 1DP* | 3DC* |
| 3 | A | A | A | B | A | B | A | B |
| 4 | A | B | B | D | D | D | D | A |
| 5 | D | D | A | B | B | D | A | B |
| 6 | A | D | A | A | B | D | A | A |
| 7 | C | C | C | C | A | B | A | A |
| 8 | C | C | C | C | B | A | D | B |
| 9 | D | D | A | D | D | D | A | D |
| 10 | A | A | B | D | A | A | A | D |
| 11 | D | D | A | D | D | D | A | B |
| 12 | A | B | A | A | A | B | A | A |
| 13 | A | A | A | A | A | B | A | A |
| 14 | C | C | C | C | C | C | C | C |
| 15 | C | C | C | C | B | B | A | A |
| 16 | C | C | C | C | C | C | C | C |
| 17 | C | C | C | C | B | B | A | A |
| 18 | C | C | C | C | B | B | A | A |
| 19 | C | C | C | C | B | B | A | A |
| 20 | C | C | C | C | C | C | C | C |
| 21 | C | C | C | C | D | B | A | A |
| 22 | A | A | A | A | A | A | A | A |
| 23 | A | A | A | A | C | C | C | C |
| 24 | A | A | A | A | A | B | A | A |
| 25 | A | A | A | A | A | A | A | A |
| 26 | A | A | A | A | C | C | C | C |
| 27 | D | D | A | A | D | D | B | B |
| 28 | A | D | A | A | A | B | A | A |
| 29 | A | A | A | A | A | B | A | A |
| 30 | C | C | C | C | B | B | A | A |
| 31 | A | A | A | A | A | B | A | A |
| 32 | C | C | C | C | B | D | B | B |
| 33 | C | C | C | C | B | D | A | B |
| 34 | C | C | C | C | A | D | A | A |
| 35 | C | C | C | C | D | D | B | B |
| 36 | C | C | C | C | B | D | B | D |
| 37 | C | C | C | C | A | D | A | B |
| 38 | C | C | C | C | B | D | A | A |
| 39 | C | C | C | C | B | D | A | B |
| 40 | C | C | C | C | D | D | D | B |
| 41 | C | C | C | C | D | D | B | B |

*Cmpd. No.—Compound Number
*PUCCRT—Wheat Brown Rust (*Puccinia triticina*)
*SEPTTR—Wheat Leaf Blotch (*Zymoseptoria tritici*)
*1DP—1 Day Protectant
*3DC—3 Day Curative
*g/H—Grams Per Hectare
*ppm—Parts Per Million

TABLE 5

Biological Activity - Disease Control at 25 ppm

| | PHAKPA* | |
|---|---|---|
| Cmpd. No. | 1DP* | 3DC* |
| 1 | A | D |
| 2 | B | D |
| 3 | D | D |
| 4 | B | D |
| 5 | D | D |
| 6 | D | D |
| 7 | D | B |
| 8 | B | D |
| 9 | D | D |
| 10 | A | B |

TABLE 5-continued

Biological Activity - Disease Control at 25 ppm

| | PHAKPA* | |
|---|---|---|
| Cmpd. No. | 1DP* | 3DC* |
| 11 | D | D |
| 12 | B | B |

*Cmpd. No.—Compound Number
*PHAKPA—Asian Soybean Rust (*Phakopsora pachyrhizi*)
*1DP—1 Day Protectant
*3DC—3 Day Curative

What is claimed is:

1. A composition for the control of a fungal pathogen including a mixture comprising:

a) one or more of the compounds of Formula I,

I 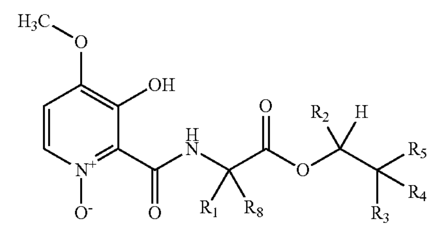 wherein:

$R_1$ is hydrogen or $C_1$-$C_5$ alkyl, each optionally substituted with 0, 1 or multiple $R_6$;

$R_2$ is hydrogen, $C_1$-$C_5$ alkyl or cycloalkyl, each optionally substituted with 0, 1 or multiple $R_6$;

$R_3$ is alkyl, cycloalkyl, aryl or heteroaryl, each optionally substituted with 0, 1 or multiple $R_6$;

$R_4$ is hydrogen, halo, hydroxyl, alkyl, or alkoxy;

$R_5$ is alkyl, cycloalkyl, aryl, heteroaryl, alkoxy, aryloxy, heteroaryloxy, each optionally substituted with 0, 1 or multiple $R_6$;

$R_6$ is hydrogen, alkyl, aryl, acyl, halo, alkoxy, or heterocyclyl, each optionally substituted with 0, 1 or multiple $R_7$;

$R_7$ is hydrogen, alkyl, aryl, acyl, halo, alkoxy, or heterocyclyl;

$R_8$ is hydrogen or $C_1$-$C_5$ alkyl, each optionally substituted with 0, 1 or multiple $R_6$; and b) a phytologically acceptable carrier material.

2. The composition according to claim 1, wherein $R_1$ and $R_8$ are independently hydrogen or $C_1$-$C_5$ alkyl.

3. The composition according to claim 2, wherein $R_2$ is $C_1$-$C_5$ alkyl.

4. The composition according to claim 2, wherein $R_3$ and $R_5$ are independently aryl, each optionally substituted with 0, 1, or multiple $R_6$.

5. The composition according to claim 2, wherein $R_4$ is hydrogen.

6. The composition according to claim 2, wherein $R_1$ and $R_8$ are independently hydrogen or $C_1$-$C_5$ alkyl, $R_2$ is $C_1$-$C_5$ alkyl, $R_3$ and $R_5$ are independently aryl, each optionally substituted with 0, 1, or multiple $R_6$, and $R_4$ is hydrogen.

7. The composition according to claim 1 wherein the fungal pathogen is one of Leaf Blotch of Wheat (*Zymoseptoria tritici*), Wheat Brown Rust (*Puccinia triticina*), Stripe Rust (*Puccinia striiformis*), Scab of Apple (*Venturia inaequalis*), Blister Smut of Maize (*Ustilago maydis*), Powdery Mildew of Grapevine (*Uncinula necator*), Barley scald (*Rhynchosporium secalis*), Blast of Rice (*Pyricularia oryzae*), Rust of Soybean (*Phakopsora pachyrhizi*), Glume Blotch of Wheat (*Leptosphaeria nodorum*), Powdery Mildew of Wheat (*Blumeria graminis* f. sp. *tritici*), Powdery Mildew of Barley (*Blumeria graminis* f. sp. *hordei*), Powdery Mildew of Cucurbits (*Erysiphe cichoracearum*), Anthracnose of Cucurbits (*Colletotrichum lagenarium*), Leaf Spot of Beet (*Cercospora beticola*), Early Blight of Tomato (*Alternaria solani*), and Net Blotch of Barley (*Pyrenophora teres*).

8. The composition according to claim 6 wherein the fungal pathogen is one of Leaf Blotch of Wheat (*Zymoseptoria tritici*), Wheat Brown Rust (*Puccinia triticina*), Scab of Apple (*Venturia inaequalis*), Barley scald (*Rhynchosporium secalis*), Blast of Rice (*Pyricularia oryzae*), Rust of Soybean (*Phakopsora pachyrhizi*), Glume Blotch of Wheat (*Leptosphaeria nodorum*), Anthracnose of Cucurbits (*Colletotrichum lagenarium*), Leaf Spot of Beet (*Cercospora beticola*), and Early Blight of Tomato (*Alternaria solani*).

9. A method for the control and prevention of fungal attack on a plant, the method including the step of:
   applying a fungicidally effective amount of at least one of the compositions of claim 6 to at least one of the plant, an area adjacent to the plant, soil adapted to support growth of the plant, a root of the plant, and foliage of the plant.

\* \* \* \* \*